United States Patent
Cao et al.

(10) Patent No.: US 12,319,659 B2
(45) Date of Patent: Jun. 3, 2025

(54) SELECTIVE LIGAND FOR DOPAMINE D3 RECEPTOR, PREPARATION METHOD THEREFOR, AND PHARMACEUTICAL APPLICATION THEREOF

(71) Applicant: Shenzhen Linglan Bio-Pharmaceutical Technology Co., Ltd, Shenzhen (CN)

(72) Inventors: Yongkai Cao, Shenzhen (CN); Zili Zhang, Shenzhen (CN); Seung Hoon Cheon, Shenzhen (CN); Kyeong Man Kim, Shenzhen (CN)

(73) Assignee: Shenzhen Linglan Bio-Pharmaceutical Technology Co., Ltd, Shenzhen (CN)

( * ) Notice: Subject to any disclaimer, the term of this patent is extended or adjusted under 35 U.S.C. 154(b) by 384 days.

(21) Appl. No.: 16/488,533

(22) PCT Filed: Feb. 11, 2018

(86) PCT No.: PCT/CN2018/076341
§ 371 (c)(1),
(2) Date: Nov. 27, 2019

(87) PCT Pub. No.: WO2018/153297
PCT Pub. Date: Aug. 30, 2018

(65) Prior Publication Data
US 2020/0087264 A1 Mar. 19, 2020

(30) Foreign Application Priority Data

Feb. 24, 2017 (KR) .................. 10-2017-0024794
Mar. 7, 2017 (CN) .................. 201710130807.0

(51) Int. Cl.
| C07D 241/04 | (2006.01) |
| A61P 15/10 | (2006.01) |
| A61P 25/00 | (2006.01) |
| A61P 25/14 | (2006.01) |
| A61P 25/16 | (2006.01) |
| A61P 25/18 | (2006.01) |
| A61P 25/30 | (2006.01) |
| C07D 401/06 | (2006.01) |

(Continued)

(52) U.S. Cl.
CPC ............ *C07D 241/04* (2013.01); *A61P 25/16* (2018.01); *C07D 401/12* (2013.01);
(Continued)

(58) Field of Classification Search
CPC .......... A61P 25/16; A61P 25/18; A61P 25/30; C07D 209/42; C07D 209/48;
(Continued)

(56) References Cited

U.S. PATENT DOCUMENTS

| 5,246,935 A | * | 9/1993 | Jeppesen | .................. | A61P 25/24 |
| | | | | | 514/254.02 |
| 5,872,119 A | | 2/1999 | Wermuth et al. | | |

(Continued)

FOREIGN PATENT DOCUMENTS

| CN | 101568524 A | 10/2009 |
| CN | 106966953 A | 7/2017 |

(Continued)

OTHER PUBLICATIONS

Kostrzewa et al., Modeling tardive dyskinesia: Predictive 5-HT2C receptor antagonist treatment, Neurotox. Res., 11, pp. 41-50 (Year: 2007).*

(Continued)

*Primary Examiner* — Jeffrey S Lundgren
*Assistant Examiner* — Alexander K. Showalter
(74) *Attorney, Agent, or Firm* — Stefan J. Kirchanski; Matthew J. Spark; Zuber Lawler LLP

(57) ABSTRACT

The present invention provides a novel ligand for the dopamine D3 receptor and a preparation method therefor. The compound, and a pharmaceutically acceptable salt and a pharmaceutical composition or a pharmaceutical preparation thereof are used for the treatment and prevention of schizophrenia, neurodegenerative diseases, particularly Parkinson's disease, drug dependence, drug addiction, anxiety, (Continued)

depression, etc. The novel ligand of the dopamine D3 receptor features a high affinity, a high specificity, and a high functional selectivity. The compound and the pharmaceutically acceptable salt and the pharmaceutical composition or the pharmaceutical preparation thereof can be used to study the distribution and function of dopamine D2 subtype receptors and mechanism of diseases associated with dysfunction of dopamine D2-like receptors, and can also be used for the disease modification of hyperprolactinemia, extrapyramidal symptoms, and levodopa-associated movement disorder or dyskinesia.

12 Claims, 4 Drawing Sheets

(51) Int. Cl.
  *C07D 401/12*   (2006.01)
  *C07D 403/06*   (2006.01)
  *C07D 403/12*   (2006.01)
  *C07D 405/12*   (2006.01)
  *C07D 409/12*   (2006.01)
  *C07D 413/12*   (2006.01)
  *C07D 417/12*   (2006.01)
(52) U.S. Cl.
  CPC ......... *C07D 403/06* (2013.01); *C07D 403/12* (2013.01); *C07D 405/12* (2013.01); *C07D 409/12* (2013.01); *C07D 413/12* (2013.01); *C07D 417/12* (2013.01)
(58) Field of Classification Search
  CPC .. C07D 215/38; C07D 241/04; C07D 277/82; C07D 401/12; C07D 403/06; C07D 403/12; C07D 405/12; C07D 409/12; C07D 413/12; C07D 417/12; G11C 11/221; G11C 11/2255; G11C 11/2273; G11C 11/2293; G11C 7/12
  See application file for complete search history.

(56) References Cited

U.S. PATENT DOCUMENTS

| | | | |
|---|---|---|---|
| 5,985,895 | A | 11/1999 | Wermuth et al. |
| 10,717,716 | B2 | 7/2020 | Lee et al. |

FOREIGN PATENT DOCUMENTS

| | | |
|---|---|---|
| JP | H03028728 A | 3/1990 |
| JP | 09278737 A | 10/1997 |
| WO | 02066468 A2 | 8/2002 |
| WO | 03028728 A1 | 4/2003 |
| WO | 2004078114 A2 | 9/2004 |
| WO | 2004099179 A1 | 11/2004 |
| WO | 2006008133 A2 | 1/2006 |
| WO | 2006072608 A2 | 7/2006 |
| WO | 2006082456 A1 | 8/2006 |
| WO | 2008142461 A1 | 11/2008 |
| WO | 2014059265 A1 | 4/2014 |

OTHER PUBLICATIONS

Stahl, Mechanism of action of pimavanserin in Parkinsonas disease psychosis: targeting serotonin 5HT2A and 5HT2C receptors, CNS Spectrums, 21, pp. 271-275 (Year: 2016).*

Beaulieu et al., Dopamine receptors—IUPHAR Review 13, British Journal of Pharmacology 172, (2015), pp. 1-23.
Das et al., Dopamine D3 Agonists in the Treatment of Parkinson's Disease, Current Topics in Medicinal Chemistry, 15 (2015), pp. 908-926.
Griffon et al., The dopamine D3 receptor and schizophrenia: pharmacological, anatomical and genetic approaches, European Neuropsychopharmacology Supplement (1995), pp. 3-9.
Heidbreder et al., Current perspectives on selective dopamine D3 receptor antagonists as pharmacotherapeutics for addictions and related disorders, Annals of the New York Academy of Sciences 1187 (2010), pp. 4-34.
Leggio et al., Current drug treatments targeting dopamine D3 receptor, Pharmacology & Therapeutics 165 (Jun. 2016) pp. 164-177.
Leggio et al., Dopamine D3 receptor as a new pharmacological target for the treatment of depression, European Journal of Pharmacology 719 (2013), pp. 25-33.
Maramai et al., Dopamine D3 Receptor Antagonists as Potential Therapeutics for the Treatment of Neurological Diseases, Frontiers in Neuroscience, vol. 10, Article 451, Oct. 5, 2016.
Yang et al., Dopamine D3 receptor: A neglected participant in Parkinson Disease pathogenesis and treatment?, Ageing Research Reviews 57 (2020) 100994.
Cao et al., "Synthesis and evaluation of arylpiperazine-reverse amides as biased dopamine D3 receptor ligands", Bioorganic & Medicinal Chemistry, 2015, vol. 23-17 pp. 5264-5272.
Capet et al., "Improving selectivity of dopamine D3 receptor ligands", Bioorganic & Medicinal Chemistry Letters, 2016, vol. 26-3, pp. 885-888.
Database Accession No. 1298630-76-8, Database Registry [Online], Chemical Abstracts Service, May 22, 2011.
Database Accession No. 1299205-46-1, Database Registry [Online], Chemical Abstracts Service, May 24, 2011.
Database Accession No. 1371183-94-6, Database Registry [Online], Chemical Abstracts Service, Apr. 30, 2012.
Database Accession No. 1623919-49-2, Database Registry [Online], Chemical Abstracts Service, Sep. 21, 2014.
Database Accession No. 292626-95-0, Database Registry [Online], Chemical Abstracts Service, Oct. 4, 2000.
Database Accession No. 899926-41-1, Database Registry [Online], Chemical Abstracts Service, Aug. 9, 2006.
Flachner et al., "Rapid in Silico Selection of an MCHR1 Antagonists' Focused Library from Multi-million Compounds' Repositories: Biological Evaluation", Medicinal Chemistry Research, 2014, vol. 23, No. 3, pp. 1234-1247.
Maruzen Co., Ltd., "Ligand", Standard Chemical Glossary, 1991, p. 654.
Nomura, "The Reactions of Imidazolides in Organic Syntheses", Journal of Synthetic Organic Chemistry, Japan, 1963, vol. 21 No. 8, pp. 585-597.
ISA/CN, International Search Report in PCT International Application No. PCT/CN2018/076341 dated May 18, 2018.
Bettinetti, L. et al., "Parallel Synthesis and Biological Screening of Dopamine Receptor ligands Taking Advantage of a Click Chemistry Based BAL Linker", Journal of Combinatorial Chemistry, 7(2), Jan. 25, 2005 (Jan. 25, 2005), ISSN: 1520-4766, pp. 309-316.
Michino, M. et al., "Toward Understanding the Structural Basis of Partial Agonism at the Dopamine D3 Receptor", Journal of Medicinal Chemistry, 60(2), Dec. 16, 2016 (Dec. 16, 2016), ISSN: 0022-2623, pp. 580-593.
Ortore, G. et al., "Different Binding Modes of Structurally Diverse Ligands for Human D3DAR", Journal of Chemical Information and Modelling, 50(12), Nov. 23, 2010 (Nov. 23, 2010), ISSN: 1549-9596, pp. 2162-2175.

* cited by examiner

SELECTIVE LIGAND FOR DOPAMINE D3 RECEPTOR, PREPARATION METHOD THEREFOR, AND PHARMACEUTICAL APPLICATION THEREOF

TECHNICAL FIELD

The present invention relates to the field of biomedical technology, and in particular to a novel dopamine D3 receptor-selective ligand, and a preparation method and medical use thereof.

BACKGROUND

Dopamine is a catecholamine neurotransmitter that is transmitted to the dopamine receptor through synapses and activates downstream signaling pathways to regulate physiological functions such as exercise, cognition, and emotion. Dopamine receptors belong to the G proteins coupled receptor family which are targeted by 30~40% of marketed targets. Based on their function and structure, dopamine receptors are mainly divided into two classes, D1-like and D2-like receptors. D1-like receptors includes D1 receptors and D5 receptors which are mainly coupled to G proteins to activate adenylate cyclase and second messengers; and D2-like receptors includes D2 receptors, D3 receptors and D4 receptors which inhibit adenylate cyclase and second messengers. D2 receptors are mainly distributed in the caudate putamen and nucleus accumbens in rodents and primates, while their distribution in other areas is low. These regions are mainly related to motor function. Compared with the distribution of D2 receptors, the distribution density of D3 receptors in corresponding regions is relatively lower. However, the distribution of D3 receptors in ventral *pallidum*, substantia nigra, thalamus and habenula is much higher than that of D2 receptors. Moreover, in the dorsal striatum, there is only the distribution of D3 receptors without that of D2 receptors. These regions are closely related to cognition and emotion. Therefore, D3 receptors are closely related to a variety of neuropsychosis, such as Parkinson's disease, sexual dysfunction, schizophrenia, drug dependence, and drug addiction. D2 receptors and D3 receptors in D2-like receptors share very high similarity and homology, so the commonly used antipsychotic drugs show low selectivity between D2 receptors and D3 receptors. Therefore, these drugs may cause some side effects such as extrapyramidal symptoms, hyperprolactinemia, etc. Among all patients who were administered with a drug and developed extrapyramidal side effects, more than 80% of them have the drug bound to D2 receptors in the brain. It is currently believed that these side effects as described above are caused by the interaction between a drug or a compound with D2 receptors. Likewise, anti-Parkinson's disease drugs cause side effects such as nausea, vomiting, mental disorders, and postural hypotension due to the low selectivity between D2 receptors and D3 receptors. Long-term use of levodopa, which is the gold standard in the treatment of Parkinson's disease, can also lead to motor dysfunction or dyskinesia. However, studies have shown that D3 receptor agonists didn't cause these side effects.

D3 receptor-selective ligands do not cause the adverse reactions as described above, and they protect and regenerate nerves by mediating brain-derived neurotrophic factors. The expression level of dopamine D3 receptors is found to be up-regulated in the mesolimbic system in the brain of patients with schizophrenia. Therefore, D3 receptor-selective inhibitors are expected to improve and treat positive symptoms of schizophrenia without causing extrapyramidal symptoms resulted from typical D2 receptor inhibitors. Inhibitors of the D3 receptor mediate the release of acetylcholine from the frontal cortex and thus contribute to regulate attention, work and social memory, i.e., to improve negative schizophrenia. Pre-clinical trials have shown that the D3 receptor-selective inhibitor 5333138 was not found to cause catalepsy within the effective dose range in antipsychotic therapy. More importantly, D3 receptor-selective ligands were not found to cause drug dependence and drug addiction compared to non-selective ligands. The D3 receptor is a target for reducing cocaine addiction and effectively treating opioid, nicotine and ethanol dependence.

Autopsy of Parkinson's disease patients has revealed that D3 receptor levels in the basal ganglia were down-regulated by 45%, while D2 receptor levels were only down-regulated by 15-25%; D3 receptor levels were down-regulated by 48% when administered with non-anti-Parkinson's disease drugs, and D3 receptor levels were up-regulated by 25% when administered with anti-Parkinson's disease drugs. Therefore, D3 receptor-selective agonists have become a new strategy for the treatment of Parkinson's disease, and D3 receptor-selective agonists can alleviate movement disorders caused by levodopa, and long-term use of D3 receptor-selective agonists can reduce movement disorders in Parkinson's disease patients. Gene knockdown of the D3 receptor causes long-term symptoms of depression and anxiety, which also suggests that D3 receptor agonists contribute to the treatment of anxiety and depression.

At present, there is a lack of highly selective dopamine D3 receptor ligands in clinical and commercial medications, as well as in molecular libraries such as Sigma-Aldrich and Selleck, which seriously hinders investigations on the distribution and function of dopamine D3 receptors. Therefore, highly selective D3 receptor ligands are molecular probes for investigating the function of dopamine D3 receptors and the pathogeny of neurological diseases associated therewith.

D3 receptor-selective ligands have not only been extensively and widely studied in academia, but have also been studied by various major pharmaceutical giants. The aza[3,1,0]bicyclohexane investigated by GlaxoSmithKline, benzenesulfonamide substituted with (piperazine) pyridine investigated by BASF and Abbott, piperidine/piperazine, benzo(pyridine)isoxazole piperazine investigated by Roche, benzomorpholine investigated by Pfizer, and chromene carboxamide investigated by Pierre Faber showed low selectivity and even no functional selectivity. Studies have shown that aripiprazole homologs UNC0006, UNC9975 and UNC9994 selectively mediated beta-arrestin signaling pathways of dopamine D2-like receptors, but showed low selectivity between D2 receptor and D3 receptor signaling pathways. German scientists have found that the o-diazole-3-formaldoxime compound 8b selectively mediated Gα protein signaling pathways of dopamine receptors, but also showed low selectivity between the D2 receptor and the D3 receptor.

One type of dopamine D3 receptor-selective ligands is 4-phenylpiperazine-amide compounds which have low water solubility and low bioavailability due to their high lipophilicity. There are also many selective ligands which are chiral compounds and difficult to separate, have high production costs, and are difficult industrially produced and thus are difficult to enter clinic.

SUMMARY

It is an object of the present disclosure to provide a novel dopamine D3 receptor-selective ligand and a preparation method thereof in view of the deficiencies in the prior art.

In one aspect, an embodiment of the present disclosure provides a novel dopamine D3 receptor-selective ligand, which comprises a major structure as follows:

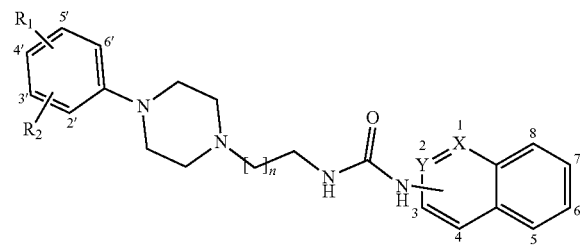

I wherein n=1 to 6;
X and Y are selected from C or N;
a urea group is located at 1- to 2-position of a naphthalene ring or at 2- to 8-position of a quinoline ring or at 1-, 3- to 8-position of an isoquinoline ring;
R1 and R2 are each independently one selected from the group consisting of H, F, Cl, $CF_3$, and OMe.

In the novel dopamine D3 receptor-selective ligand provided by the present disclosure, n=1 to 4.

In the novel dopamine D3 receptor-selective ligand provided by the present disclosure, a urea group is located at 2-, 3-, 6-, 7-position of a quinoline ring.

In the novel dopamine D3 receptor-selective ligand provided by the present disclosure, the urea group is located at 3-, 6-, 7-position of an isoquinoline ring.

In the novel dopamine D3 receptor-selective ligand provided by the present disclosure, the major structure is one selected from the group consisting of
1-(4-(4-(2,3-dichlorophenyl)piperazin-1-yl)butyl)-3-(quinolin-3-yl)urea;
1-(4-(4-(2,4-dichlorophenyl)piperazin-1-yl)butyl)-3-(quinolin-3-yl)urea;
1-(4-(4-(4-chlorophenyl)piperazin-1-yl)butyl)-3-(quinolin-3-yl)urea;
1-(4-(4-(3-chlorophenyl)piperazin-1-yl)butyl)-3-(quinolin-3-yl)urea;
1-(4-(4-(2-chlorophenyl)piperazin-1-yl)butyl)-3-(quinolin-3-yl)urea;
1-(4-(4-(2-fluorophenyl)piperazin-1-yl)butyl)-3-(quinolin-3-yl)urea;
1-(4-(4-(2,3-difluorophenyl)piperazin-1-yl)butyl)-3-(quinolin-3-yl)urea;
1-(4-(4-(2,4-difluorophenyl)piperazin-1-yl)butyl)-3-(quinolin-3-yl)urea;
1-(4-(4-(2,6-difluorophenyl)piperazin-1-yl)butyl)-3-(quinolin-3-yl)urea;
1-(4-(4-(4-chloro-2-fluorophenyl)piperazin-1-yl)butyl)-3-(quinolin-3-yl)urea;
1-(4-(4-(3-(trifluoromethyl)phenyl)piperazin-1-yl)butyl)-3-(quinolin-3-yl)urea;
1-(4-(4-(2-fluoro-5-(trifluoromethyl)phenyl)piperazin-1-yl)butyl)-3-(quinolin-3-yl)urea;
1-(4-(4-(4-chlorophenyl)piperazin-1-yl)butyl)-3-(quinolin-2-yl)urea; 1-(4-(4-(4-chlorophenyl)piperazin-1-yl)butyl)-3-(isoquinolin-3-yl)urea.

In the novel dopamine D3 receptor-selective ligand provided by the present disclosure, the novel dopamine D3 receptor-selective ligand has high affinity, high specificity and high functional selectivity.

In the novel dopamine D3 receptor-selective ligand provided by the present disclosure, the novel dopamine D3 receptor-selective ligand selectively mediates signaling pathways downstream of D3 receptor.

Correspondingly, the present disclosure also provides a method for preparing the novel dopamine D3 receptor-selective ligand as described above, comprising the following steps:

(1) mixing a piperazine compound with N-(bromoalkyl) phthalimide, $K_2CO_3$ and NaI in acetonitrile and refluxing for 8-12 hours to synthesize piperazine-phthalimide, wherein the reaction scheme is as follows:

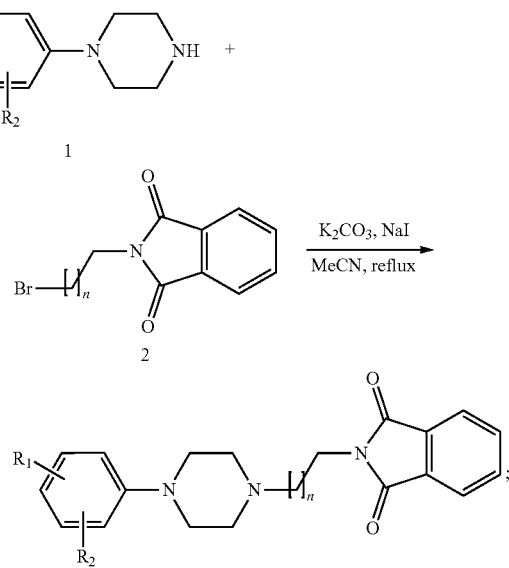

(2) deprotecting the piperazine-phthalimide, or reacting the piperazine with an aliphatic amine bearing a leaving group and then deprotecting, or reacting the piperazine with bromocarbonitrile and then reducing to an amine to furnish piperazine-aliphatic amine, wherein the reaction scheme is as follows:

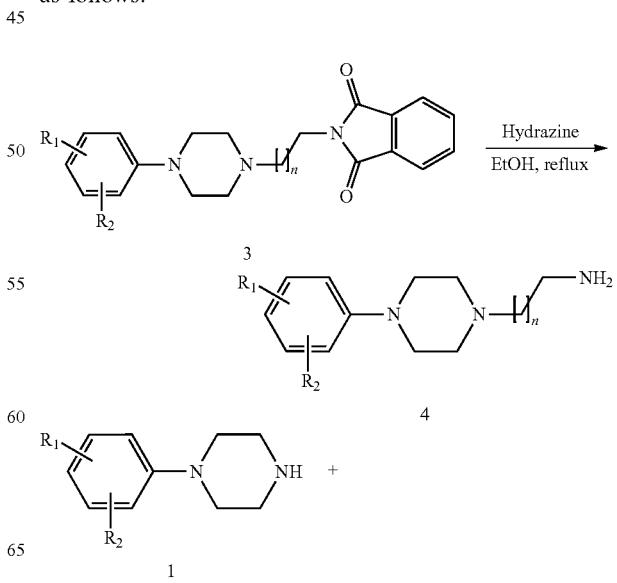

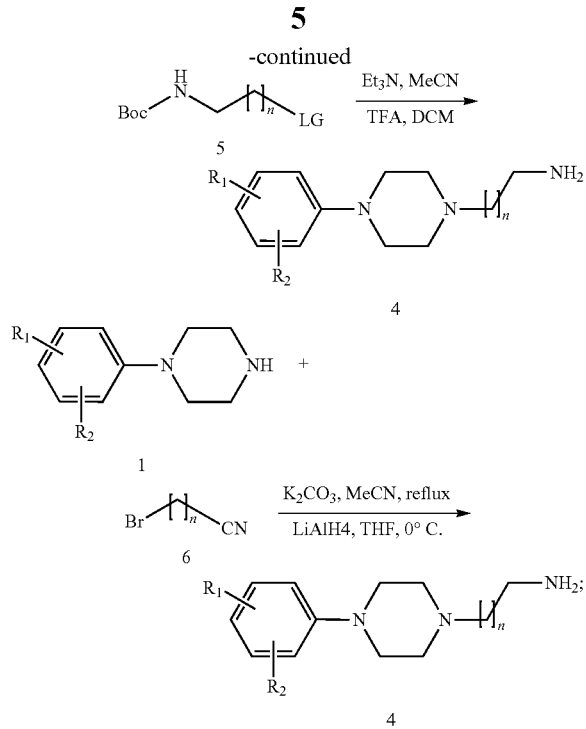

(3) the coupling of the piperazine-aliphatic amine to an aromatic amine via CDI or oxalyl chloride or triphosgene to produce the novel dopamine D3 receptor-selective ligand according to claim 1, wherein the reaction scheme is as follows:

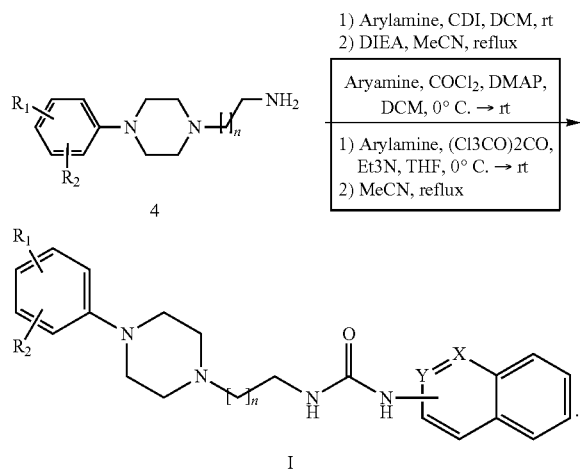

In the preparation method provided by the present disclosure, the molar ratio of the piperazine compound, N-(bromoalkyl)phthalimide, $K_2CO_3$ and NaI in step (1) is 1:1.05:3:0.3.

In the preparation method provided by the present disclosure, deprotecting the piperazine-phthalimide to produce piperazine-aliphatic amine in step (2) includes: dissolving the piperazine-phthalimide in absolute ethanol, adding hydrazine hydrate, and reacting for 6-8 hours, wherein the molar ratio of piperazine-phthalimide to hydrazine hydrate is 1:3.

Reacting the piperazine with an aliphatic amine bearing a leaving group and then de-protecting to produce piperazine-aliphatic amine in step (2) includes: dissolving the piperazine, an aliphatic amine bearing a leaving group, and triethylamine in acetonitrile, refluxing for 8-12 hours, evaporating the solvent to dry, and then performing flash chromatography, adding piperazine-aliphatic amine to dichloromethane, and trifluoroacetic acid, raising the temperature slowly to room temperature, and reacting for 5 hours, wherein the molar ratio of piperazine, aliphatic amine, triethylamine, and trifluoroacetic acid is 1:1:3:20.

Reacting the piperazine with bromocarbonitrile and then reducing to an amine to obtain piperazine-aliphatic amine in step (2) includes: mixing the piperazine, bromocarbonitrile, and $K_2CO_3$ in acetonitrile, refluxing for 8-12 hours, filtering, recovering the solvent, and performing flash chromatography; dissolving the product piperazine-aliphatic amine in THF, adding dropwise to a solution of lithium aluminum hydride in THF, and raising the temperature slowly to room temperature, wherein the molar ratio of piperazine, bromocarbonitrile, $K_2CO_3$, and lithium aluminum hydride is 1:1.05:3:2.

In the preparation method provided by the present disclosure, producing the novel dopamine D3 receptor-selective ligand as described above via carbodiimide (CDI) includes: adding a solution of aromatic amine in dichloromethane dropwise to a solution of CDI in dichloromethane, reacting at room temperature for 6-8 hours, evaporating the solvent to dry, dissolving the residue in acetonitrile together with piperazine-aliphatic amine and DIEA, and reacting under reflux for 6-8 hours, wherein the molar ratio of piperazine-aliphatic amine, aromatic amine, CDI, and DIEA is 1:1:1.4:1.6.

Producing the novel dopamine D3 receptor-selective ligand as described above via oxalyl chloride includes: adding a solution of DMAP in dichloromethane dropwise to a mixture of a solution of oxalyl chloride in toluene and a solution of piperazine-aliphatic amine in dichloromethane, reacting at room temperature for 16-20 hours, evaporating the solvent to dry, dissolving the residue in acetonitrile together with piperazine-aliphatic amine, and refluxing for 6-8 hours, wherein the molar ratio of piperazine-aliphatic amine, aromatic amine, oxalyl chloride, and DAMP is 1:1:1.2:0.05-0.1;

Producing the novel dopamine D3 receptor-selective ligand as described above via triphosgene includes: under nitrogen, adding a solution of aromatic amine in THF dropwise to a solution of triphosgene in THF, slowly adding triethylamine, reacting at room temperature for 8-12 hours, evaporating the solvent to dry, dissolving the residue in acetonitrile together with piperazine-aliphatic amine, and refluxing for 6-8 hours, wherein the molar ratio of piperazine-aliphatic amine, aromatic amine, triphosgene, and triethylamine is 1:1:1.2:2.

Correspondingly, the present disclosure further provides a novel dopamine D3 receptor-selective ligand, which comprises a major structure as follows:

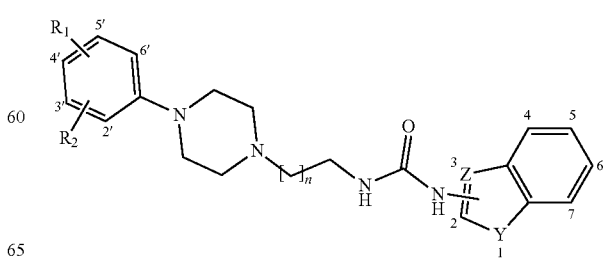

wherein n=1 to 6;
Y is selected from NH or O or S; Z is selected from C or N
a urea group is located at 2-position, 4- to 7-position of a benzo 5-membered heterocyclic ring;
R1 and R2 are each independently one selected from the group consisting of H, F, Cl, $CF_3$ and OMe.

In the novel dopamine D3 receptor-selective ligand provided by the present disclosure, n=1 to 4.

In the novel dopamine D3 receptor-selective ligand provided by the present disclosure, a urea group is located at 2-position, 5-position, 6-position of the benzo 5-membered heterocyclic ring.

In the novel dopamine D3 receptor-selective ligand provided by the present disclosure, the major structure is one selected from the group consisting of
1-(benzothiazol-2-yl)-3-(4-(4-(2,3-dichlorophenyl)piperazin-1-yl)butyl)urea;
1-(benzothiazol-2-yl)-3-(4-(4-(2,4-dichlorophenyl)piperazin-1-yl)butyl)urea;
1-(benzothiazol-2-yl)-3-(4-(4-(4-chlorophenyl)piperazin-1-yl)butyl)urea;
1-(benzothiazol-2-yl)-3-(4-(4-(3-(trifluoromethyl)phenyl)piperazin-1-yl)butyl)urea.

In the novel dopamine D3 receptor-selective ligand provided by the present disclosure, the novel dopamine D3 receptor-selective ligand has high affinity, high specificity and high functional selectivity.

In the novel dopamine D3 receptor-selective ligand provided by the present disclosure, the novel dopamine D3 receptor-selective ligand selectively mediates signaling pathways downstream of the D3 receptor.

Provided is pharmaceutical use of the novel dopamine D3 receptor-selective ligand as described above, wherein the ligand, pharmaceutical salt, pharmaceutical composition or a pharmaceutical preparation thereof, are useful for preventing or treating central nervous system diseases.

Provided is pharmaceutical use of the novel dopamine D3 receptor-selective ligand as described above, wherein the central nervous system diseases include neurodegenerative diseases preferably Parkinson's disease, schizophrenia, anxiety, depression, drug addiction and drug dependence.

Provided is pharmaceutical use of the novel dopamine D3 receptor-selective ligand as described above, wherein the novel dopamine D3 receptor-selective ligand is used in molecular probes and tool drugs.

Provided is pharmaceutical use of the novel dopamine D3 receptor-selective ligand as described above, wherein the novel dopamine D3 receptor-selective ligand are useful for the investigation of the distribution and function of dopamine D2-like subtype receptors, and for the prevention or treatment of diseases associated with its dysfunction.

Provided is pharmaceutical use of the novel dopamine D3 receptor-selective ligand as described above, wherein the ligand, pharmaceutical salt, pharmaceutical composition or a pharmaceutical preparation thereof, are useful for ameliorating hyperprolactinemia, extrapyramidal symptoms, and levodopa-related movement disorders and dyskinesia.

Correspondingly, the present disclosure further provides a therapeutic pharmaceutical preparation comprising the novel dopamine D3 receptor-selective ligand as described above, and a pharmaceutical carrier.

The embodiments of the present disclosure have the following beneficial effects: novel dopamine D3 receptor-selective ligands provided by the present disclosure and pharmaceutical salts thereof are useful for the treatment and prevention of neurodegenerative diseases, especially Parkinson's disease, schizophrenia, drug dependence, drug addiction, anxiety, depression, etc. Studies have shown that the novel dopamine D3 receptor-selective ligands specifically bind to D3 receptors and selectively mediate D3 receptors. Such compounds and pharmaceutical salts thereof are useful for investigating the distribution and function of dopamine receptors and diseases associated with their dysfunction.

DESCRIPTION OF THE DRAWINGS

The drawings to be used in the description of the examples or the prior art will be briefly described below, in order to illustrate the technical solutions of the examples of the present disclosure or the prior art more clearly. The drawings in the following description are only examples of the invention, and other drawings may be obtained by those skilled in the art without creative work.

DETAILED DESCRIPTION

Figure 1:
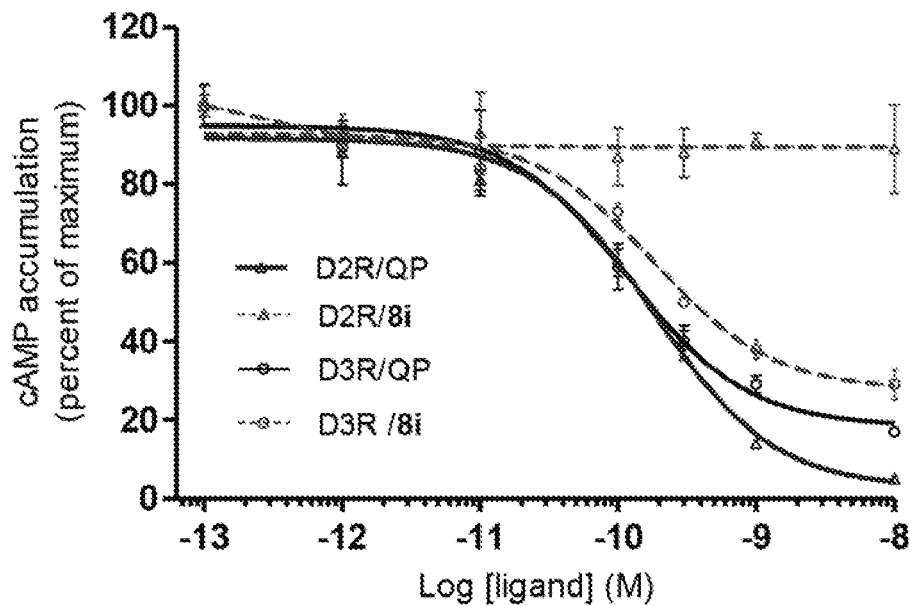
FIG. 1 shows the intrinsic functional dose-effect curve of D3 receptor-specific ligand 8i according to an example of the present disclosure.
Figure 1:
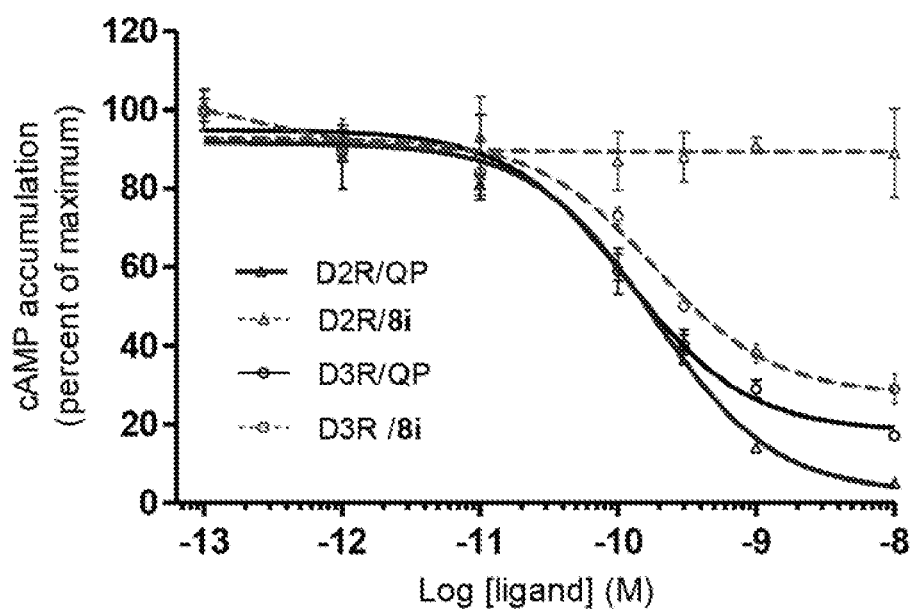
Figure 2:
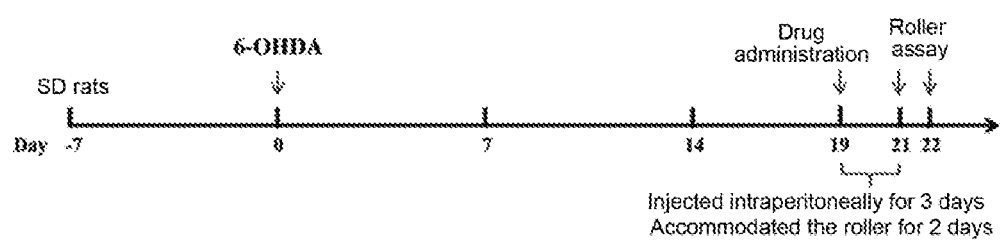
FIG. 2 shows the scheme of the rotarod assay.
Figure 3:
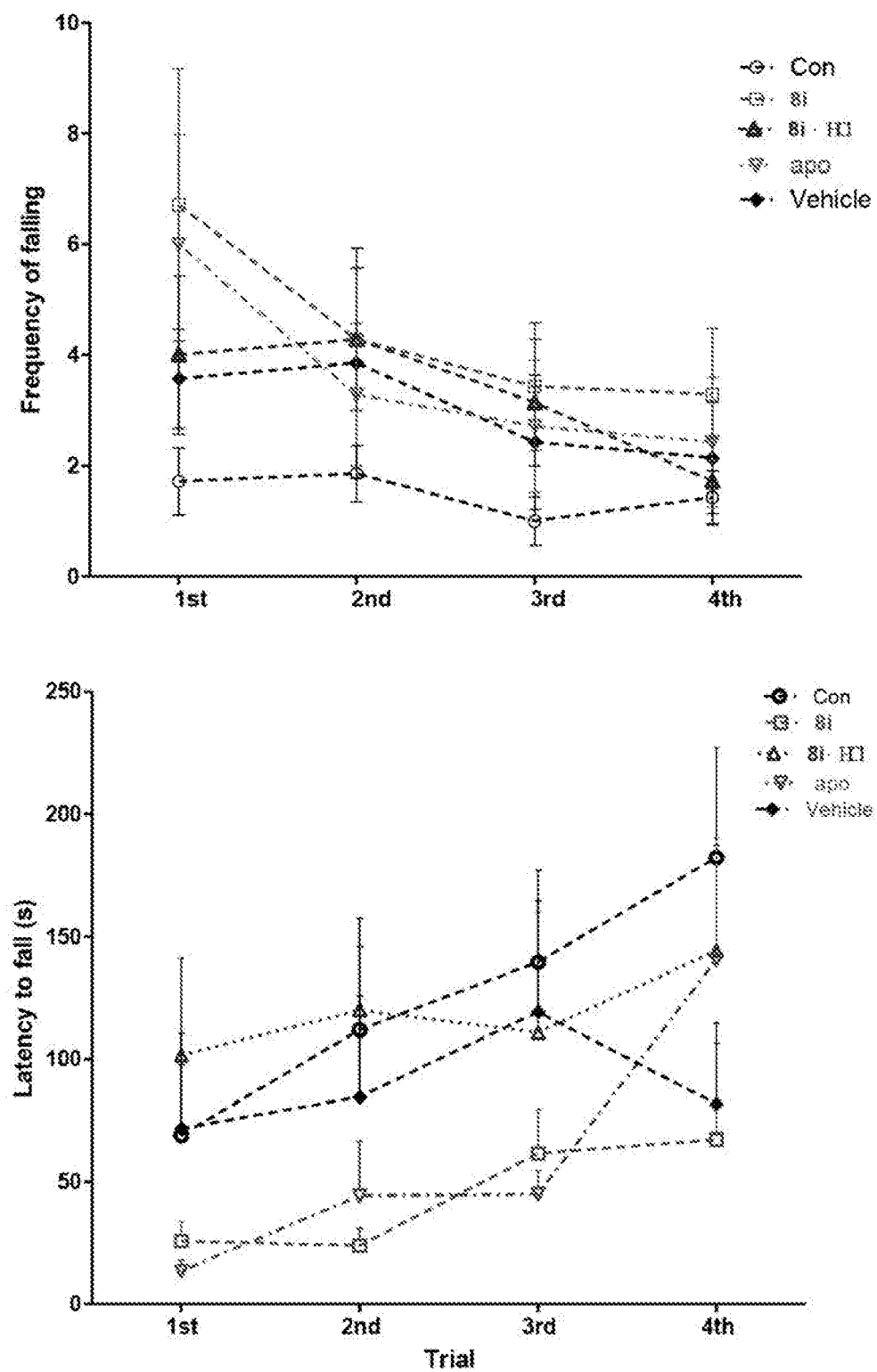
FIG. 3 shows the time-effect diagram of compound 8i and its hydrochloride on the rotarod assay in 6-OHDA-induced Parkinson's disease rats.
Figure 4:
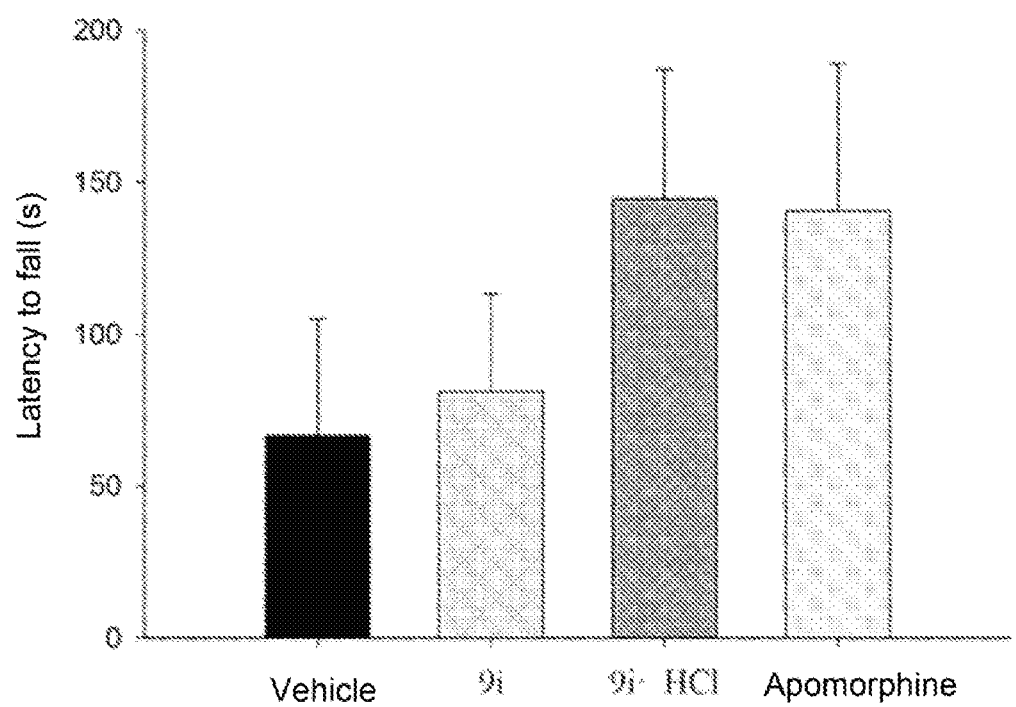
FIG. 4 shows the effect of compound 8i and its hydrochloride on latency in 6-OHDA-induced Parkinson's disease rats.

The technical solutions in the examples of the present disclosure will be described, clearly and completely in combination with the drawings in the examples of the present disclosure. The described examples are only part of the present disclosure rather than all. All other examples obtained by those ordinary skilled in the art under the premise of no creative work, on the basis of examples of the present disclosure, are within the scope of the present disclosure.

The present disclosure provides a novel dopamine D3 receptor-selective ligand, comprising a major structure as follows:

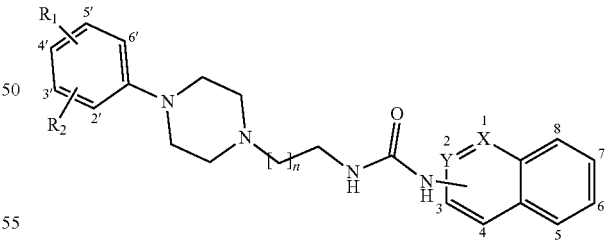

I wherein n=1 to 6. Preferably, in an example of the present disclosure, n=1 to 4, i.e., the intermediate chain may be ethyl, propyl, butyl, pentyl. X and Y are selected from C or N, i.e., the aromatic group to which the urea group is attached may be naphthalene, quinoline, isoquinoline. Preferably, in an example of the present disclosure, the aromatic group to which the urea group is attached is quinoline and isoquinoline. The urea group is located at the 2-position of the naphthalene ring or at the 2- to 8-position of the quinoline ring or at the 1-, 3- to 8-position of isoquinoline.

Preferably, the urea group is located at 2-, 3-, 6-, 7-position of the quinoline ring or at 3-, 6-, 7-position of isoquinoline. Preferably, in an example of the present disclosure, the urea group is located at 2-, 3-position of quinoline or at the 3-position of isoquinoline. R1 and R2 are each independently one selected from the group consisting of H, F, Cl, CF$_3$ and OMe.

The present disclosure further provides another novel dopamine D3 receptor-selective ligand, comprising a major structure as follows:

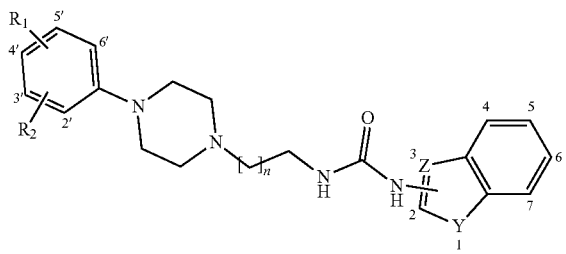

wherein n=1 to 6, preferably n=1 to 4, i.e., the intermediate chain may be ethyl, propyl, butyl, pentyl. Preferably, in an example of the present disclosure, the intermediate chain is butyl. Y is selected from NH or O or S; and Z is selected from C or N; i.e., the aromatic group is benzimidazole, benzothiazole, benzoxazole, indole, benzofuran and benzothiophene. The urea group is located at 2-position, 5-position, 6-position of a benzo 5-membered heterocyclic ring. Preferably, in an example of the present disclosure, the aromatic group to which the urea group is attached is benzimidazole, and the urea group is located at the 2-position of benzimidazole. R1 and R2 are each independently one selected from the group consisting of H, F, Cl, CF$_3$ and OMe.

The present disclosure further provides a pharmaceutical salt comprising a non-toxic salt generated from the novel dopamine D3 receptor-selective ligand as described above in the form of a free alkaloid with an organic or inorganic acid. The pharmaceutical salt may be a salt of an inorganic acid including but not limited to hydrochloric acid, HBr, sulfuric acid and phosphoric acid, a salt of an organic acid including but not limited to acetic acid, propionic acid, pyruvic acid, butyric acid, alpha-/beta-/gamma-hydroxybutyric acid, valeric acid, hydroxyvaleric acid, caproic acid, hydroxycaproic acid, caprylic acid, capric acid, lauric acid, myristic acid, palmitic acid, stearic acid, lactic acid, D-glucuronic acid, D-galacturonic acid, glycine, benzoic acid, hydroxybenzoic acid, gallic acid, salicylic acid, vanillic acid, coumaric acid, caffeic acid, orotic acid, tartaric acid, malic acid, oxalic acid, malonic acid, succinic acid, maleic acid, oxalacetic acid, glutamic acid, aspartic acid, citric acid, isocitric acid, methanesulfonic acid, toluenesulfonic acid and trifluoromethanesulfonic acid.

The novel dopamine D3 receptor-selective ligand provided by the present disclosure is a D3 receptor ligand having high affinity, high specificity and high functional selectivity. "High affinity" means that the Ki value in the binding of the ligand to human dopamine D3 receptor in a radioligand assay is preferably no higher than 20 nM. "High specificity" means that the Ki value in the binding of the ligand to human D2 receptor is at least 100 times of the Ki value in the binding of the ligand to human D3 receptor in a radioligand assay. "Highly functional selectivity" means that the ligand selectively activates signaling pathways of a D3 receptor, but doesn't activate signaling pathways of homologous proteins D2 receptors and D4 receptors in a luciferase reporter assay.

D3 receptor ligand molecules which had a high-affinity of nanomolar level or even subnanomolar level and which had a selectivity for D2 receptors of more than 10,000-fold were preferably screened by the present disclosure through a radioligand assay. In comparison, arylpiperazine-arylamide ligand molecules having an extremely high selectivity as reported in literature showed a selectivity of only 13- or 59-fold in our test system. Agonists, partial agonists, antagonists of a D3 receptor that selectively (partially) activated signaling pathways downstream of the D3 receptor without activating signaling pathways downstream of D2 receptors and D4 receptors were preferably screened through a luciferase reporter assay. Therefore, such compounds can be used as molecular probes and tool drugs for investigating the physiological distribution and function of D2 receptor and D3 receptor, and diseases associated with their functional disorders and dopamine metabolic disorders. A "diseases associated with D3 receptor dysfunction" refers to diseases caused directly or indirectly by dopamine D3 receptor dysfunction, such as schizophrenia, cognitive disorders, Parkinson's disease, emotional/motivational disorders, drug dependence, drug addiction, anxiety, sleep disorders and male sexual dysfunction, etc.

The present disclosure further provides a pharmaceutical composition or a dosage form comprising at least one novel dopamine D3 receptor-selective ligand as described above, or a pharmaceutical salt thereof, and a pharmaceutical carrier or excipient thereof, such as nano drug delivery system. Preferred D3 receptor-selective ligands or a plurality of drug compositions or pharmaceutical preparations thereof may be used to treat neurodegenerative diseases, especially Parkinson's disease, schizophrenia, cognitive impairment, emotional/motivational disorders, anxiety, depression, drug addiction, drug dependence. The D3 receptor-selective ligand or a plurality of drug combinations or pharmaceutical preparations thereof according to the present disclosure can also be used to improve D2 receptor-related hyperprolactinosis, extrapyramidal symptoms such as rigidity, akathisia, dystonia, pseudoparkinsonism and to improve movement disorders or dyskinesia caused by long-term use of levodopa.

In general, in addition to at least one preferred D3 receptor ligand, the therapeutic pharmaceutical preparations of the present disclosure at least further comprise a pharmaceutical carrier or excipient. The pharmaceutical dosage form may be a tablet, a capsule, a dropping pill, an aerosol, a pill, a powder, a mixture, an emulsion, a granule, a liposome, a transdermal agent, a buccal agent, a lyophilized powder injection, etc., and it may be ordinary formulations, sustained release formulations, controlled release formulations, and various microparticle delivery systems. The pharmaceutical carrier may be a conventional diluent, absorbent, wetting agent, binder, disintegrant, lubricant, flavoring agent, etc., or it may be a novel nano drug delivery system including nanoparticles, nanotubes, and nano core-shell microcapsules, etc.

The present disclosure further provides a method for preparing a novel dopamine D3 receptor-selective ligand, comprising the following steps:

(1) mixing a piperazine compound with N-(bromoalkyl) phthalimide, K$_2$CO$_3$ and NaI in acetonitrile and refluxing for 8-12 hours to produce piperazine-phthalimide, wherein the reaction scheme is as follows:

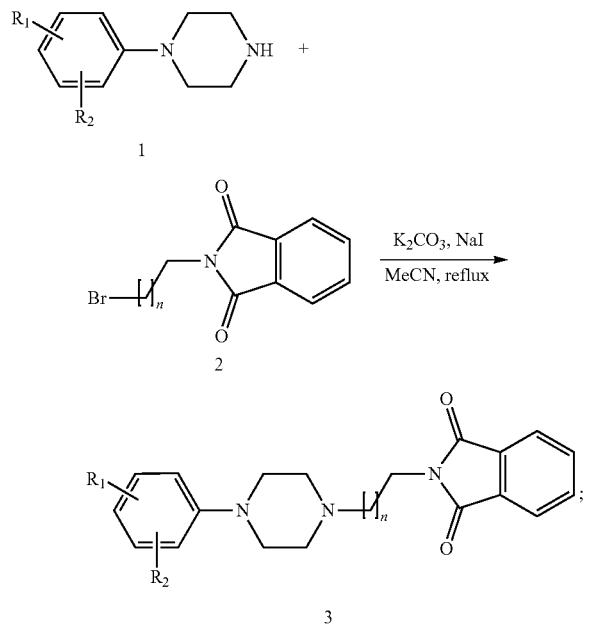

preferably, the molar ratio of the piperazine compound, N-(bromoalkyl)phthalimide, $K_2CO_3$ and NaI is 1:1.05:3:0.3;

(2) deprotecting the piperazine-phthalimide, or reacting the piperazine-phthalimide with an aliphatic amine bearing a leaving group and then de-protecting, or reacting the piperazine-phthalimide with bromocarbonitrile and then reducing to an amine to produce piperazine-aliphatic amine, wherein the reaction formula is as follows:

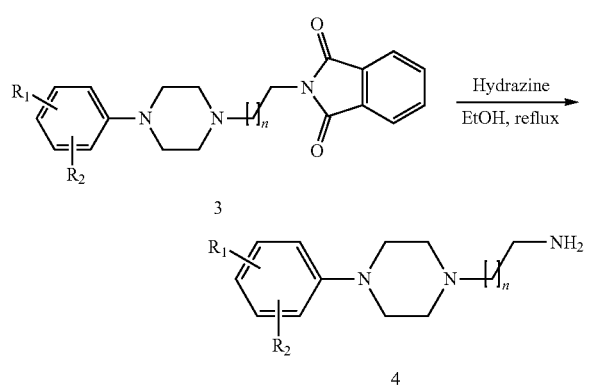

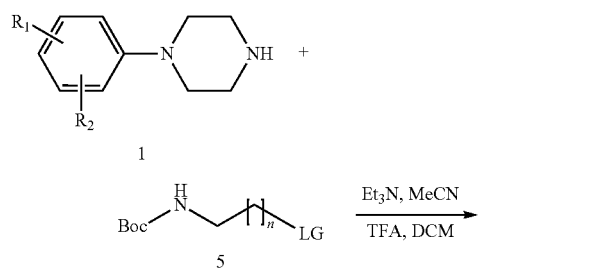

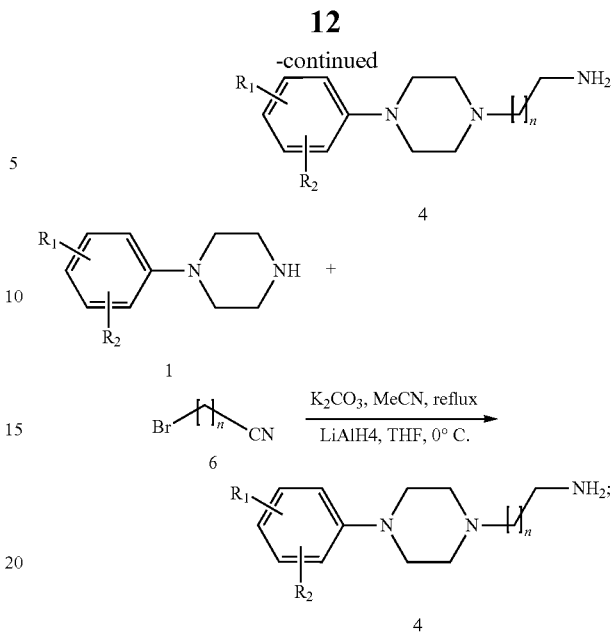

preferably, deprotecting the piperazine-phthalimide to produce piperazine-aliphatic amine includes: dissolving the piperazine-phthalimide in absolute ethanol, adding hydrazine hydrate, and reacting for 6-8 hours, wherein the molar ratio of piperazine-phthalimide to hydrazine hydrate is 1:3; reacting the piperazine with an aliphatic amine bearing a leaving group and then de-protecting to produce piperazine-aliphatic amine includes: dissolving the piperazine, an aliphatic amine bearing a leaving group, and triethylamine in acetonitrile, refluxing for 8-12 hours, evaporating the solvent to dry, and then performing flash chromatography, adding the product piperazine-aliphatic amine to dichloromethane, adding trifluoroacetic acid, raising the temperature slowly to room temperature, and reacting for 5 hours, wherein the molar ratio of piperazine-phthalimide, aliphatic amine, triethylamine, and trifluoroacetic acid is 1:1:3:20; reacting the piperazine with bromocarbonitrile and then reducing to an amine to produce piperazine-aliphatic amine includes: mixing the piperazine, bromocarbonitrile, and $K_2CO_3$ in acetonitrile, refluxing for 8-12 hours, filtering, recovering the solvent, and performing flash chromatography; dissolving the piperazine-aliphatic amine bearing Boc group in THF, adding dropwise to a solution of lithium aluminum hydride in THF, and raising the temperature slowly to room temperature, wherein the molar ratio of piperazine-aliphatic amine, bromocarbonitrile, $K_2CO_3$, and lithium aluminum hydride is 1:1.05:3:2;

(3) coupling the piperazine-aliphatic amine to an aromatic amine via CDI or oxalyl chloride or triphosgene to produce the novel dopamine D3 receptor-selective ligand according to claim 1, wherein the reaction formula is as follows:

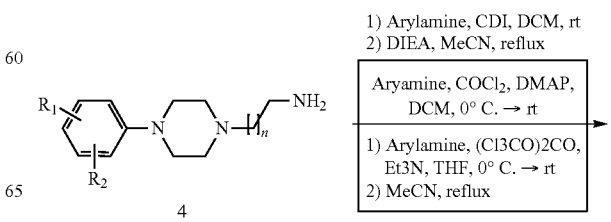

-continued

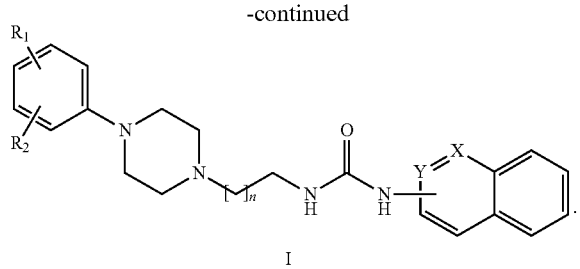

I preferably, producing the novel dopamine D3 receptor-selective ligand as described above via CDI includes: adding a solution of aromatic amine in dichloromethane dropwise to a solution of CDI in dichloromethane, reacting at room temperature for 6-8 hours, evaporating the solvent to dry, dissolving the residue in acetonitrile together with piperazine-aliphatic amine and DIEA, and reacting under reflux for 6-8 hours, wherein the molar ratio of piperazine-aliphatic amine, aromatic amine, CDI, and DIEA is 1:1:1.4:1.6; producing the novel dopamine D3 receptor-selective ligand according to claim 1 via oxalyl chloride includes: adding a solution of DMAP in dichloromethane dropwise to a mixture of a solution of oxalyl chloride in toluene and a solution of piperazine-aliphatic amine in dichloromethane, reacting at room temperature for 16-20 hours, evaporating the solvent to dry, dissolving the residue in acetonitrile together with piperazine-aliphatic amine, and refluxing for 6-8 hours, wherein the molar ratio of piperazine-aliphatic amine, aromatic amine, oxalyl chloride, and DAMP is 1:1:1.2:0.05-0.1; producing the novel dopamine D3 receptor-selective ligand as described above via triphosgene includes: under nitrogen, adding a solution of aromatic amine in THF dropwise to a solution of triphosgene in THF, slowly adding triethylamine, reacting at room temperature for 8-12 hours, evaporating the solvent to dry, dissolving the residue in acetonitrile together with piperazine-aliphatic amine, and refluxing for 6-8 hours, wherein the molar ratio of piperazine-aliphatic amine, aromatic amine, triphosgene, and triethylamine is 1:1:1.2:2.

The preparation of the novel dopamine D3 receptor-selective ligand of the present disclosure is described in detail below.

Step S1: Synthesis of Arylpiperazine-phthalimide

Aniline and bis(2-chloroethyl)amine hydrochloride were mixed in diethylene glycol monomethyl ether (DGME), and refluxed for 6-8 hours. Appropriate amounts of methanol and diethyl ether were added for recrystallization to obtain arylpiperazine. The arylpiperazine and 1.05 molar equivalent of N-(4-bromobutyl)phthalimide, 3 molar equivalent of $K_2CO_3$ and 0.3 molar equivalent of NaI were mixed in acetonitrile, reacted under reflux for 6-8 hours, and filtered. The solvent was recovered and the residue was separated by column chromatography to obtain arylpiperazine-phthalimide. The reaction formula was as follows:

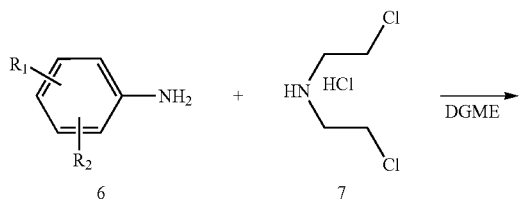

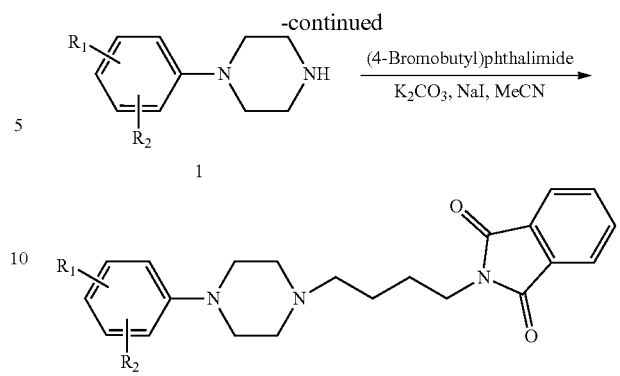

3a-3r

| | |
|---|---|
| a: $R_1$ = 2-F, $R_2$ = H | j: $R_1$ = 2-Cl, $R_2$ = 3-Cl |
| b: $R_1$ = 3-F, $R_2$ = H | k: $R_1$ = 2-Cl, $R_2$ = 4-Cl |
| c: $R_1$ = 4-F, $R_2$ = H | l: $R_1$ = 2-Cl, $R_2$ = 6-Cl |
| d: $R_1$ = 2-F, $R_2$ = 3-F | m: $R_1$ = 2-F |
| e: $R_1$ = 3-F, $R_2$ = 4-F | n: $R_1$ = 2,3-diCl |
| f: $R_1$ = 4-F, $R_2$ = 6-F | o: $R_1$ = 2,3-diCl |
| g: $R_1$ = 2-Cl, $R_2$ = H | p: $R_1$ = 3-CF$_3$ |
| h: $R_1$ = 3-Cl, $R_2$ = H | q: $R_1$ = 4-Cl |
| i: $R_1$ = 4-Cl, $R_2$ = H | r: $R_1$ = 3-Cl |

Test results are as follows.

2-(4-(4-(2-fluorophenyl)piperazin-1-yl)butyl)isoindoline-1,3-dione (3a)

Compound 3a was a light yellow crystal. Rf=0.182 ($CH_2Cl_2$/EtOAc=1:1). Yield: 90.3%. Mp: 120-122° C. $^1$H NMR (400 MHz, CDCl$_3$) δ 7.84 (dd, J=5.46, 3.03 Hz, 2H), 7.71 (dd, J=5.44, 3.05 Hz, 2H), 7.09-6.97 (m, 2H), 6.97-6.87 (m, 2H), 3.73 (t, J=7.10 Hz, 2H), 3.20-3.02 (m, 4H), 2.62 (d, J=4.25 Hz, 4H), 2.50-2.35 (m, 2H), 1.73 (dd, J=14.81, 7.41 Hz, 2H), 1.66-1.48 (m, 2H). $^{13}$C NMR (101 MHz, CDCl$_3$) δ 168.42, 155.69 (d, $J_{CF}$=245.86 Hz), 140.15 (d, $J_{CF}$=8.50 Hz), 133.89, 132.11, 124.41 (d, $J_{CF}$=3.55 Hz), 123.16, 122.33 (d, $J_{CF}$=7.97 Hz), 118.87 (d, $J_{CF}$=3.03 Hz), 116.04 (d, $J_{CF}$=20.82 Hz), 58.02, 53.26, 50.52, 50.49, 37.84, 26.58, 24.19.

2-(4-(4-(4-fluorophenyl)piperazin-1-yl)butyl)isoindoline-1,3-dione (3c)

Compound 3c was prepared as a colorless crystal. Rf=0.125 ($CH_2Cl_2$/EtOAc=1:1). Yield: 86.9%. Mp: 116-118° C. $^1$H NMR (400 MHz, CDCl$_3$) δ 7.84 (dd, J=5.45, 3.04 Hz, 2H), 7.71 (dd, J=5.46, 3.04 Hz, 2H), 7.02-6.90 (m, 2H), 6.91-6.79 (m, 2H), 3.73 (t, J=7.10 Hz, 2H), 3.16-3.03 (m, 4H), 2.68-2.53 (m, 4H), 2.49-2.34 (m, 2H), 1.74 (dt, J=14.86, 7.46 Hz, 2H), 1.65-1.47 (m, 2H). $^{13}$C NMR (101 MHz, CDCl$_3$) δ 168.48, 158.31, 155.94, 148.00 (d, $J_{CF}$=2.22 Hz), 133.94, 132.13, 123.21, 117.73 (d, $J_{CF}$=7.59 Hz), 115.48 (d, $J_{CF}$=22.14 Hz), 58.00, 53.24, 50.15, 37.86, 26.61, 24.22.

2-(4-(4-(2,3-fluorophenyl)piperazin-1-yl)butyl)isoindoline-1,3-dione (3d)

Compound 3d was a colorless solid. Rf=0.265 ($CH_2Cl_2$/EtOAc=1:1). Yield: 87.7%. Mp: 101-103° C. $^1$H NMR (400 MHz, CDCl$_3$) δ 7.83 (td, J=5.27, 5.27, 2.09 Hz, 2H), 7.72 (td, J=5.44, 5.24, 2.09 Hz, 2H), 6.95 (tdd, J=8.17, 5.88, 2.00

Hz, 1H), 6.82-6.71 (m, 1H), 6.72-6.62 (m, 1H), 3.72 (dd, J=13.32, 6.23 Hz, 2H), 3.19-3.03 (m, 4H), 2.71-2.54 (m, 4H), 2.48-2.39 (m, 2H), 1.74 (dt, J=14.91, 7.41 Hz, 2H), 1.65-1.49 (m, 2H). $^{13}$C NMR (101 MHz, CDCl$_3$) δ 168.45, 151.51 (dd, J=245.74, 11.96 Hz), 143.96 (dd, J=247.0, 13.73 Hz), 141.98 (d, J=5.62 Hz), 133.93, 132.11, 123.55 (dd, J=8.53, 4.89 Hz), 123.19, 113.67, 109.87 (d, J=17.69 Hz), 57.98, 53.16, 50.45, 50.42, 37.84, 26.58, 24.18.

2-(4-(4-(2,4-fluorophenyl)piperazin-1-yl)butyl)isoindoline-1,3-dione (3e)

Compound 3e was a colorless solid. Rf=0.156 (CH$_2$Cl$_2$/EtOAc=1:1). Yield: 66.0%. Mp: 101-103° C. $^1$H NMR (400 MHz, CDCl$_3$) δ 7.84 (dd, J=5.44, 3.05 Hz, 2H), 7.72 (dd, J=5.44, 3.05 Hz, 2H), 6.95-6.84 (m, 1H), 6.85-6.73 (m, 2H), 3.79-3.67 (m, 2H), 3.13-2.93 (m, 4H), 2.61 (s, 4H), 2.50-2.37 (m, 2H), 1.83-1.66 (m, 2H), 1.66-1.47 (m, 2H). $^{13}$C NMR (101 MHz, CDCl$_3$) δ 168.43, 157.81 (dd, J$_{CF}$=11.78, 242.94 Hz), 155.57 (dd, J$_{CF}$=11.23, 249.15 Hz), 136.75 (dd, J=8.95, 3.35 Hz), 133.91, 132.11, 123.17, 119.35 (dd, J=9.25, 4.25 Hz), 110.62 (dd, J=21.32, 3.72 Hz), 104.62 (dd, J=25.81, 0.89 Hz), 57.98, 53.23, 50.88 (d, J=2.55 Hz), 37.83, 26.58, 24.17.

2-(4-(4-(2,6-fluorophenyl)piperazin-1-yl)butyl)isoindoline-1,3-dione (3f)

Compound 3f was a colorless solid. Rf=0.265 (CH$_2$Cl$_2$/EtOAc=1:1). Yield: 60.2%. Mp: 102-103° C. $^1$H NMR (300 MHz, CDCl$_3$) δ 7.90-7.78 (m, 2H), 7.76-7.66 (m, 2H), 6.89 (td, J=9.64, 9.27, 5.80 Hz, 1H), 6.84-6.71 (m, 2H), 3.73 (t, J=7.04 Hz, 2H), 3.14-2.94 (m, 4H), 2.72-2.52 (m, 4H), 2.50-2.35 (m, 2H), 1.75 (dt, J=14.30, 6.91 Hz, 2H), 1.58 (ddd, J=14.90, 8.16, 4.43 Hz, 2H).

2-(4-(4-(2-chlorophenyl)piperazin-1-yl)butyl)isoindoline-1,3-dione (3g)

Compound 3g was a light yellow solid. Rf=0.242 (CH$_2$Cl$_2$/EtOAc=1:1). Yield: 73.1%. Mp: 141-143° C. $^1$H NMR (400 MHz, CDCl$_3$) δ 7.84 (dd, J=5.43, 3.05 Hz, 2H), 7.71 (dd, J=5.45, 3.04 Hz, 2H), 7.15 (t, J=8.12 Hz, 1H), 6.86 (t, J=2.12 Hz, 1H), 6.78 (ddd, J=8.90, 4.92, 1.77 Hz, 2H), 3.73 (t, J=7.10 Hz, 2H), 3.24-3.08 (m, 4H), 2.63-2.50 (m, 4H), 2.48-2.35 (m, 2H), 1.73 (dd, J=14.87, 7.44 Hz, 2H), 1.66-1.48 (m, 2H). $^{13}$C NMR (101 MHz, CDCl$_3$) δ 168.45, 152.33, 134.90, 133.93, 132.11, 129.99, 123.20, 119.15, 115.65, 113.79, 57.96, 53.03, 48.61, 37.83, 26.58, 24.19.

2-(4-(4-(3-chlorophenyl)piperazin-1-yl)butyl)isoindoline-1,3-dione (3h)

Compound 3h was a light yellow solid. Rf=0.25 (CH$_2$Cl$_2$/EtOAc=1:1). Yield: 75%. Mp: 111-112° C. $^1$H NMR (400 MHz, CDCl$_3$) δ 7.84 (dd, J=5.45, 3.04 Hz, 2H), 7.71 (dd, J=5.46, 3.04 Hz, 2H), 7.34 (dd, J=7.89, 1.50 Hz, 1H), 7.25-7.16 (m, 1H), 7.03 (dd, J=8.06, 1.46 Hz, 1H), 6.95 (td, J=7.78, 1.51 Hz, 1H), 3.81-3.67 (m, 2H), 3.06 (s, 4H), 2.63 (s, 4H), 2.51-2.38 (m, 2H), 1.74 (dt, J=14.85, 7.51 Hz, 2H), 1.66-1.50 (m, 2H). $^{13}$C NMR (101 MHz, CDCl$_3$) δ 168.42, 149.29, 133.88, 132.11, 130.58, 128.72, 127.54, 123.57, 123.16, 120.33, 58.02, 53.35, 51.18, 37.85, 26.60, 24.23.

2-(4-(4-(4-chlorophenyl)piperazin-1-yl)butyl)isoindoline-1,3-dione (3i)

Compound 3i was a light yellow solid. Rf=0.234 (CH$_2$Cl$_2$/EtOAc=1:1). Yield: 73.8%. Mp: 138-141° C. $^1$H NMR (400 MHz, CDCl$_3$) δ 7.85 (dd, J=5.37, 3.10 Hz, 2H), 7.74 (dd, J=5.48, 3.02 Hz, 2H), 7.27-7.10 (m, 2H), 6.90-6.76 (m, 2H), 3.73 (t, J=6.98 Hz, 2H), 3.26-3.12 (m, 4H), 2.69 (s, 4H), 2.59-2.43 (m, 2H), 1.73 (dd, J=14.17, 7.09 Hz, 2H), 1.68-1.56 (m, 2H). $^{13}$C NMR (101 MHz, CDCl$_3$) δ 172.62, 153.47, 138.07, 135.84, 132.86, 128.90, 127.18, 121.43, 61.71, 56.73, 52.65, 41.52, 30.37, 27.40.

2-(4-(4-(2,3-dichlorophenyl)piperazin-1-yl)butyl)isoindoline-1,3-dione (3j)

Compound 3i was a colorless solid. Rf=0.136 (CH$_2$Cl$_2$/EtOAc=1:1). Yield: 77.7%. Mp: 121-123° C. $^1$H NMR (400 MHz, CDCl$_3$) δ 7.84 (dd, J=5.45, 3.04 Hz, 2H), 7.71 (dd, J=5.45, 3.05 Hz, 2H), 7.20-7.09 (m, 2H), 6.94 (dd, J=6.39, 3.20 Hz, 1H), 3.73 (t, J=7.10 Hz, 2H), 3.05 (s, 4H), 2.62 (s, 4H), 2.49-2.39 (m, 2H), 1.74 (dt, J=14.86, 7.47 Hz, 2H), 1.64-1.51 (m, 2H). $^{13}$C NMR (101 MHz, CDCl$_3$) δ 168.45, 151.30, 133.98, 133.91, 132.13, 127.42, 124.50, 123.19, 118.58, 57.97, 53.28, 51.30, 37.86, 26.60, 24.22.

2-(4-(4-(2,4-dichlorophenyl)piperazin-1-yl)butyl)isoindoline-1,3-dione (3k)

Compound 3k was a colorless solid. Yield: 76.5%. Mp: 106-107° C. $^1$H NMR (400 MHz, CDCl$_3$) δ 7.84 (dd, J=5.44, 3.04 Hz, 2H), 7.71 (dd, J=5.44, 3.05 Hz, 2H), 7.34 (d, J=2.43 Hz, 1H), 7.17 (dd, J=8.61, 2.45 Hz, 1H), 6.95 (d, J=8.64 Hz, 1H), 3.73 (t, J=7.11 Hz, 2H), 3.02 (s, 4H), 2.61 (s, 4H), 2.50-2.37 (m, 2H), 1.73 (dd, J=14.84, 7.44 Hz, 2H), 1.65-1.49 (m, 2H). $^{13}$C NMR (101 MHz, CDCl$_3$) δ 168.45, 148.12, 133.92, 132.14, 130.27, 129.42, 128.08, 127.59, 123.19, 121.12, 57.97, 53.25, 51.20, 37.87, 26.60, 24.22.

2-(4-(4-(4-chloro-2-fluorophenyl)piperazin-1-yl)butyl)isoindoline-1,3-dione (3m)

Compound 3m was a light yellow solid. Rf=0.219 (CH$_2$Cl$_2$/EtOAc=1:1). Yield: 75.2%. Mp: 89-91° C. $^1$H NMR (400 MHz, CDCl$_3$) δ 7.83 (dd, J=5.45, 3.05 Hz, 2H), 7.71 (dd, J=5.45, 3.04 Hz, 2H), 7.10-6.93 (m, 2H), 6.84 (t, J=8.75 Hz, 1H), 3.73 (t, J=7.09 Hz, 2H), 3.16-2.97 (m, 4H), 2.60 (d, J=3.98 Hz, 4H), 2.49-2.37 (m, 2H), 1.73 (dd, J=14.91, 7.43 Hz, 2H), 1.64-1.49 (m, 2H). $^{13}$C NMR (101 MHz, CDCl$_3$) δ 168.38, δ 155.25 (d, J=249.82 Hz), 139.01 (d, J=8.60 Hz), 133.89, 132.09, 126.56 (d, J=10.03 Hz), 124.45 (d, J=3.52 Hz), 123.15, 119.50 (d, J=3.85 Hz), 116.74 (d, J=24.30 Hz), 57.94, 53.11, 50.46, 50.42, 37.82, 26.56, 24.16.

2-(4-(4-(2-fluoro-5-(trifluoromethyl)phenyl)piperazin-1-yl)butyl)isoindoline-1,3-dione (3n)

Compound 3n was a colorless solid. Rf=0.617 (CH$_2$Cl$_2$/EtOAc=1:1). Yield: 87.5%. $^1$H NMR (300 MHz, CDCl$_3$) δ 7.92-7.79 (m, 2H), 7.76-7.66 (m, 2H), 7.23-7.01 (m, 3H), 3.73 (t, J=7.05 Hz, 2H), 3.24-3.02 (m, 4H), 2.72-2.54 (m, 4H), 2.51-2.33 (m, 2H), 1.73 (dd, J=14.34, 7.33 Hz, 2H), 1.58 (dd, J=14.85, 8.70 Hz, 2H).

2-(4-(4-(3-(trifluoromethyl)phenyl)piperazin-1-yl)butyl)isoindoline-1,3-dione (3p)

Compound 3k was a colorless solid. Rf=0.219 (n-hexane/EtOAc=1:1). Yield: 86.9%. Mp: 96-98° C. $^1$H NMR (400 MHz, CDCl$_3$) δ 7.84 (dd, J=5.47, 3.02 Hz, 2H), 7.71 (dd, J=5.45, 3.05 Hz, 2H), 7.33 (t, J=7.95 Hz, 1H), 7.10 (s, 1H), 7.08-7.00 (m, 2H), 4.12 (q, J=7.15 Hz, 1H), 3.73 (t, J=7.11 Hz, 2H), 3.31-3.13 (m, 4H), 2.70-2.50 (m, 4H), 2.49-2.38 (m, 2H), 1.75 (dt, J=14.90, 7.47 Hz, 2H), 1.68-1.48 (m, 2H), 1.26 (t, J=7.14 Hz, 1H). $^{13}$C NMR (101 MHz, CDCl$_3$) δ 168.44, 151.39, 133.92, 132.14, 131.37 (q, J$_{CF}$=31.67 Hz), 129.50, 124.35 (dd, J$_{CF}$=271.92 Hz), 123.19, 118.58, 115.68 (q, J$_{CF}$=3.73 Hz), 112.07 (q, J$_{CF}$=3.88 Hz), 60.39, 57.92, 53.01, 48.61, 37.83, 26.56, 24.17, 21.04, 14.20.

Step S2: Synthesis of arylpiperazine-aliphatic amine by one of the following three methods. The reaction formula was as follows.

(1) The arylpiperazine-phthalimide was dissolved in absolute ethanol, and 3 molar equivalent of hydrazine hydrate was added. The mixture was reacted at 60° C. for 6-8 hours, and the reaction was detected by TLC. The crude product was used directly in the next step.

(2) The arylpiperazine, 1 molar equivalent of 4-(Boc-amino)butyl methanesulfonate, and 3 molar equivalent of triethylamine were dissolved in acetonitrile, and refluxed for 8-12 hours. The solvent was evaporated to dry and the residue was separated by column chromatography. The product arylpiperazine-aliphatic amine (Boc-protected) was added into dichloromethane, and 20 molar equivalent of trifluoroacetic acid was added at 0° C. The temperature was slowly raised to room temperature, and reacted for 5 hours. The reaction was detected by thin layer chromatography (TLC). The crude product was used directly in the next step.

(3) The arylpiperazine, 1.05 molar equivalent of bromo-carbonitrile, and 3 molar equivalent of K$_2$CO$_3$ were mixed in acetonitrile, refluxed for 8-12 hours, and filtered. The solvent was recovered and the residue was subjected to column chromatography. The product arylpiperazine-phthalimide was dissolved in THF, and added dropwise into a solution of 2 molar equivalent of lithium aluminum hydride in THF at 0° C. The temperature was slowly raised to room temperature, and the reaction was detected by TLC. The crude product was used directly in the next step.

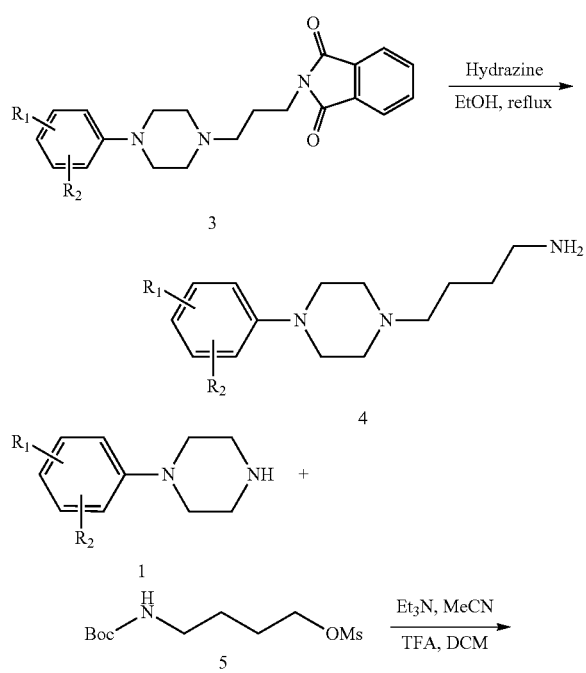

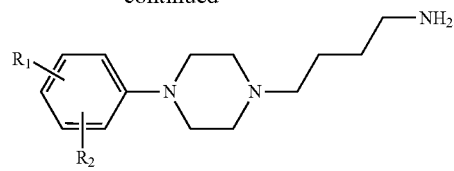

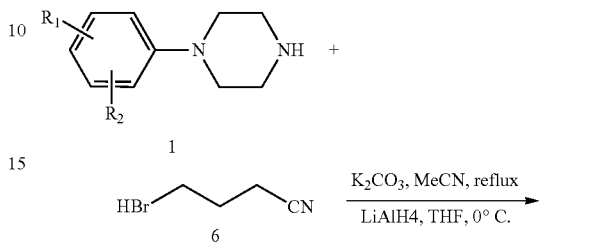

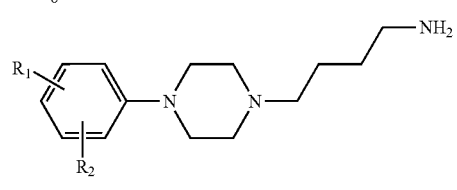

| | |
|---|---|
| a: R$_1$ = 2-F, R$_2$ = H | j: R$_1$ = 2-Cl, R$_2$ = 3-Cl |
| b: R$_1$ = 3-F, R$_2$ = H | k: R$_1$ = 2-Cl, R$_2$ = 4-Cl |
| c: R$_1$ = 4-F, R$_2$ = H | l: R$_1$ = 2-Cl, R$_2$ = 6-Cl |
| d: R$_1$ = 2-F, R$_2$ = 3-F | m: R$_1$ = 2-F |
| e: R$_1$ = 3-F, R$_2$ = 4-F | n: R$_1$ = 2,3-diCl |
| f: R$_1$ = 4-F, R$_2$ = 6-F | o: R$_1$ = 2,3-diCl |
| g: R$_1$ = 2-Cl, R$_2$ = H | p: R$_1$ = 3-CF$_3$ |
| h: R$_1$ = 3-Cl, R$_2$ = H | q: R$_1$ = 4-Cl |
| i: R$_1$ = 4-Cl, R$_2$ = H | r: R$_1$ = 3-Cl |

Step S3: Synthesis of Arylpiperazine-arylurea

A solution of aromatic amine in dichloromethane was added dropwise into a solution of 1.6 molar equivalent of CDI in dichloromethane, and reacted at room temperature for 6-8 hours. The solvent was evaporated to dry. 1 molar equivalent of arylpiperazine-aliphatic amine and 1.6 molar equivalent of DIEA were dissolved in acetonitrile, and reacted under reflux for 6-8 hours. The reaction was detected by TLC. After the reaction was completed, the solvent was recovered to dry, and the residue was dispersed with ethyl acetate, washed with saturated sodium chloride, and the organic layer was separated. The solvent was recovered to dry, and the residue was separated by column chromatography.

Wherein, dopamine D3 receptor-selective ligands having the major structure of Formula I were obtained by the following reaction formula:

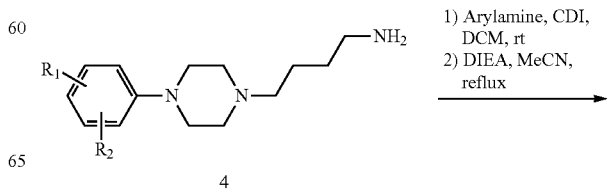

-continued

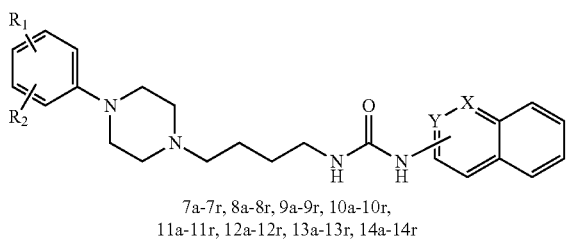

7a-7r, 8a-8r, 9a-9r, 10a-10r,
11a-11r, 12a-12r, 13a-13r, 14a-14r

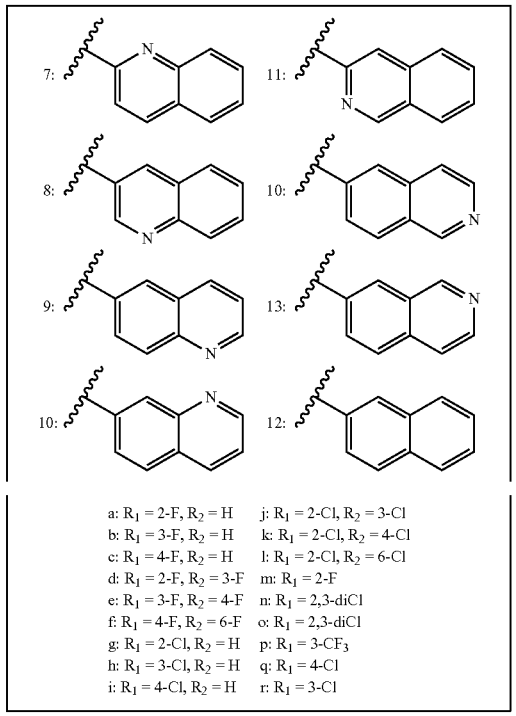

a: $R_1$ = 2-F, $R_2$ = H     j: $R_1$ = 2-Cl, $R_2$ = 3-Cl
b: $R_1$ = 3-F, $R_2$ = H     k: $R_1$ = 2-Cl, $R_2$ = 4-Cl
c: $R_1$ = 4-F, $R_2$ = H     l: $R_1$ = 2-Cl, $R_2$ = 6-Cl
d: $R_1$ = 2-F, $R_2$ = 3-F   m: $R_1$ = 2-F
e: $R_1$ = 3-F, $R_2$ = 4-F   n: $R_1$ = 2,3-diCl
f: $R_1$ = 4-F, $R_2$ = 6-F   o: $R_1$ = 2,3-diCl
g: $R_1$ = 2-Cl, $R_2$ = H    p: $R_1$ = 3-$CF_3$
h: $R_1$ = 3-Cl, $R_2$ = H    q: $R_1$ = 4-Cl
i: $R_1$ = 4-Cl, $R_2$ = H    r: $R_1$ = 3-Cl

Dopamine D3 receptor-selective ligands having the major structure of Formula II were obtained by the following reaction formula:

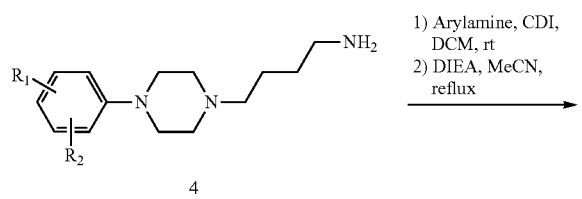

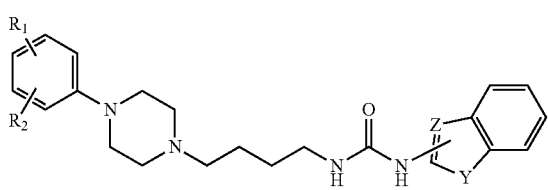

15a-15r, 16a-16r, 17a-17r, 18a-18r, 19a-19r, 20a-20r,
21a-21r, 22a-22r, 23a-23r, 24a-24r, 25a-25r, 26a-26r

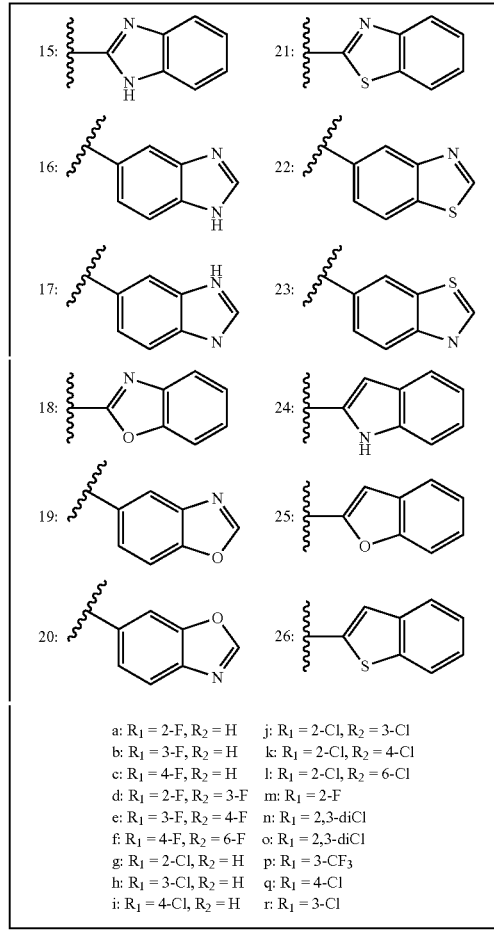

a: $R_1$ = 2-F, $R_2$ = H     j: $R_1$ = 2-Cl, $R_2$ = 3-Cl
b: $R_1$ = 3-F, $R_2$ = H     k: $R_1$ = 2-Cl, $R_2$ = 4-Cl
c: $R_1$ = 4-F, $R_2$ = H     l: $R_1$ = 2-Cl, $R_2$ = 6-Cl
d: $R_1$ = 2-F, $R_2$ = 3-F   m: $R_1$ = 2-F
e: $R_1$ = 3-F, $R_2$ = 4-F   n: $R_1$ = 2,3-diCl
f: $R_1$ = 4-F, $R_2$ = 6-F   o: $R_1$ = 2,3-diCl
g: $R_1$ = 2-Cl, $R_2$ = H    p: $R_1$ = 3-$CF_3$
h: $R_1$ = 3-Cl, $R_2$ = H    q: $R_1$ = 4-Cl
i: $R_1$ = 4-Cl, $R_2$ = H    r: $R_1$ = 3-Cl

Further, the dopamine D3 receptor-selective ligand having the major structure of Formula I was one selected from the group consisting of:

1-(4-(4-(4-chlorophenyl)piperazin-1-yl)butyl)-3-(quinolin-2-yl)urea (7i)

$^1$H NMR (400 MHz, MeOD) δ 8.06 (d, J=8.8 Hz, 1H), 7.81-7.70 (m, 2H), 7.65 (ddd, J=8.4, 7.0, 1.4 Hz, 1H), 7.42 (ddd, J=8.1, 7.0, 1.1 Hz, 1H), 7.24-7.15 (m, 2H), 7.03 (d, J=8.8 Hz, 1H), 6.89-6.79 (m, 2H), 3.48 (s, 2H), 3.24-3.08 (m, 4H), 2.75-2.61 (m, 4H), 2.53 (t, J=7.0 Hz, 2H), 1.84-1.62 (m, 4H).

$^{13}$C NMR (101 MHz, MeOD) δ 156.39, 152.17, 149.67, 145.25, 138.53, 130.06, 128.84, 127.59, 126.45, 124.82, 124.58, 117.39, 113.22, 58.15, 52.88, 48.86, 39.43, 27.72, 23.93.

1-(4-(4-(2-fluorophenyl)piperazin-1-yl)butyl)-3-(quinolin-3-yl)urea (8a)

$^1$H NMR (300 MHz, CD$_3$OD) δ 8.66 (d, J=2.4 Hz, 1H), 8.47 (d, J=2.4 Hz, 1H), 7.91 (d, J=8.3 Hz, 1H), 7.75 (dd, J=8.2, 1.3 Hz, 1H), 7.52 (dddd, J=16.2, 14.7, 6.9, 1.4 Hz, 2H), 7.12-6.85 (m, 4H), 3.37-3.23 (m, 3H), 3.20-3.03 (m, 4H), 2.84-2.64 (m, 4H), 2.61-2.42 (m, 2H), 1.62 (dd, J=10.0, 5.7 Hz, 4H). $^{13}$C NMR (75 MHz, CDCl$_3$) δ 155.61 (d, J$_{CF}$=245.8 Hz), 156.03, 143.93, 139.68 (d, J$_{CF}$=8.6 Hz), 133.35, 128.60, 128.33, 127.55, 127.46, 127.17, 124.45 (d, $J_{CF}$=3.5 Hz), 122.66 (d, $J_{CF}$=8.0 Hz), 122.16, 118.85 (d, $J_{CF}$=2.96 Hz), 116.08 (d, $J_{CF}$=20.7 Hz), 57.92, 53.06, 50.10, 39.86, 27.84, 23.81.

1-(4-(4-(2,3-difluorophenyl)piperazin-1-yl)butyl)-3-(quinolin-3-yl)urea (8d)

$^1$H NMR (500 MHz, CDCl$_3$: CD$_3$OD 8:1) δ 8.57 (d, J=2.4 Hz, 1H), 8.50 (d, J=2.5 Hz, 1H), 7.89 (d, J=8.3 Hz, 1H), 7.76-7.69 (m, 1H), 7.55-7.47 (m, 1H), 7.47-7.40 (m, 1H), 6.99-6.86 (m, 1H), 6.79-6.68 (m, 1H), 6.64 (t, J=7.8 Hz, 1H), 3.26 (d, J=6.5 Hz, 2H), 3.16-3.02 (m, 4H), 2.65 (d, J=4.3 Hz, 4H), 2.49-2.34 (m, 2H), 1.63-1.46 (m, 4H). $^{13}$C NMR (126 MHz, CDCl$_3$: CD$_3$OD 8:1) δ 156.10, 151.43 (dd, $J_{CF}$=246.3, 12.1 Hz), 143.94 (dd, $J_{CF}$=247.0, 13.8 Hz), 143.48, 143.39, 143.36, 141.42 (dd, $J_{CF}$=3.7, 2.0 Hz), 133.70, 128.75, 127.92, 127.43, 127.34, 127.09, 126.62 (dd, $J_{CF}$=4.8, 3.7 Hz), 121.62 (d, $J_{CF}$=13.4 Hz), 113.71, 110.27 (d, $J_{CF}$=17.7 Hz), 58.06, 52.98, 49.91, 49.88, 39.34, 27.70, 23.53.

1-(4-(4-(2,4-difluorophenyl)piperazin-1-yl)butyl)-3-(quinolin-3-yl)urea (8e)

$^1$H NMR (300 MHz, CDCl$_3$: CD$_3$OD 1:1) δ 8.68 (d, J=2.5 Hz, 1H), 8.52 (d, J=2.4 Hz, 1H), 7.95 (d, J=8.3 Hz, 1H), 7.83-7.74 (m, 1H), 7.67-7.47 (m, 2H), 7.06-6.91 (m, 1H), 6.84 (ddd, J=12.5, 7.0, 2.8 Hz, 2H), 3.38-3.27 (m, 2H), 3.20-3.01 (m, 4H), 2.71 (s, 4H), 2.51 (t, J=7.2 Hz, 2H), 1.75-1.51 (m, 4H). $^{13}$C NMR (75 MHz, CDCl$_3$:CD$_3$OD 1:1) δ 157.82 (dd, $J_{CF}$=245.4, 12.1 Hz), 155.26 (dd, $J_{CF}$=249.0, 12.1 Hz), 156.10, 143.29, 143.01, 135.88, 133.52, 128.46, 127.33, 127.22, 127.02, 126.88, 119.34 (dd, $J_{CF}$=9.3, 4.2 Hz), 110.34 (dd, $J_{CF}$=21.3, 4.0 Hz), 104.16 (t, $J_{CF}$=24.8 Hz), 57.84, 52.71, 50.07, 39.18, 27.63, 23.23.

1-(4-(4-(2,6-difluorophenyl)piperazin-1-yl)butyl)-3-(quinolin-3-yl)urea (8f)

$^1$H NMR (300 MHz, CDCl$_3$) δ 8.66 (d, J=2.5 Hz, 1H), 8.51 (d, J=2.2 Hz, 1H), 8.46 (s, 1H), 7.94 (d, J=8.3 Hz, 1H), 7.68 (dd, J=8.1, 1.3 Hz, 1H), 7.58-7.38 (m, 2H), 6.90-6.67 (m, 3H), 3.29 (t, J=6.2 Hz, 2H), 3.10-2.92 (m, 4H), 2.62 (s, 4H), 2.40 (t, J=6.9 Hz, 2H), 1.55 (d, J=3.8 Hz, 4H).

$^{13}$C NMR (75 MHz, CDCl$_3$) δ 158.38 (dd, $J_{CF}$=243.5, 11.7 Hz), 156.13, 155.53 (dd, $J_{CF}$=249.6, 11.7 Hz), 153.96, 143.95, 136.21 (dd, $J_{CF}$=9.1, 3.0 Hz), 133.42, 128.61, 128.33, 127.55, 127.44, 127.18, 122.14, 119.43 (dd, $J_{CF}$=9.2, 4.1 Hz), 110.70 (dd, $J_{CF}$=21.3, 3.9 Hz), 104.67 (t, $J_{CF}$=24.5 Hz), 57.78, 52.98, 50.32, 39.75, 27.76, 23.63.

1-(4-(4-(2-chlorophenyl)piperazin-1-yl)butyl)-3-(quinolin-3-yl)urea (8g)

$^1$H NMR (600 MHz, CDCl$_3$) δ 8.66 (d, J=2.5 Hz, 1H), 8.53 (d, J=2.4 Hz, 1H), 8.34 (s, 1H), 7.95 (d, J=8.4 Hz, 1H), 7.70 (dd, J=8.2, 1.0 Hz, 1H), 7.53 (ddd, J=8.4, 6.9, 1.4 Hz, 1H), 7.50-7.41 (m, 1H), 7.34 (dd, J=7.8, 1.2 Hz, 1H), 7.23-7.15 (m, 1H), 6.96 (dd, J=12.0, 4.5 Hz, 2H), 3.30 (t, J=6.6 Hz, 2H), 3.07 (s, 4H), 2.67 (s, 3H), 2.50-2.38 (m, 2H), 1.66-1.57 (m, 2H), 1.55 (dd, J=13.4, 6.7 Hz, 2H).

$^{13}$C NMR (151 MHz, CDCl$_3$) δ 156.07, 148.72, 143.97, 133.43, 130.61, 128.66, 128.63, 128.38, 127.61, 127.50, 127.46, 127.15, 123.92, 122.07, 120.30, 57.83, 53.13, 50.59, 39.74, 27.73, 23.67.

1-(4-(4-(3-chlorophenyl)piperazin-1-yl)butyl)-3-(quinolin-3-yl)urea (8h)

$^1$H NMR (300 MHz, CDCl$_3$) δ 8.65 (d, J=2.5 Hz, 1H), 8.50 (d, J=1.6 Hz, 2H), 7.94 (d, J=8.3 Hz, 1H), 7.74-7.63 (m, 1H), 7.58-7.39 (m, 2H), 7.14 (t, J=8.3 Hz, 1H), 6.81 (dd, J=5.0, 2.8 Hz, 2H), 6.71 (dd, J=9.2, 1.5 Hz, 1H), 3.29 (d, J=6.2 Hz, 2H), 3.21-3.03 (m, 4H), 2.63-2.46 (m, 4H), 2.36 (t, J=7.0 Hz, 2H), 1.52 (s, 4H). $^{13}$C NMR (126 MHz, CDCl$_3$) δ 156.16, 151.97, 144.00, 143.96, 134.94, 133.45, 130.05, 128.64, 128.34, 127.61, 127.47, 127.23, 122.21, 119.51, 115.76, 113.89, 57.77, 52.75, 48.20, 39.80, 27.80, 23.70.

1-(4-(4-(4-chlorophenyl)piperazin-1-yl)butyl)-3-(quinolin-3-yl)urea (8i)

$^1$H NMR (300 MHz, DMSO-d$_6$) δ 8.90 (s, 1H), 8.76 (d, J=2.6 Hz, 1H), 8.44 (d, J=2.5 Hz, 1H), 7.95-7.74 (m, 2H), 7.61-7.41 (m, 2H), 7.28-7.10 (m, 2H), 6.92 (d, J=9.1 Hz, 2H), 6.42 (t, J=5.6 Hz, 1H), 3.23-3.03 (m, 6H), 2.50 (dt, J=3.6, 1.8 Hz, 4H), 2.35 (t, J=5.9 Hz, 2H), 1.50 (s, 4H).

$^{13}$C NMR (75 MHz, DMSO-d$_6$) δ 155.26, 149.81, 144.11, 143.20, 134.44, 128.57, 128.48, 128.26, 127.18, 126.83, 126.65, 122.23, 119.13, 116.72, 57.44, 52.56, 47.97, 27.65, 23.65.

1-(4-(4-(2,3-dichlorophenyl)piperazin-1-yl)butyl)-3-(quinolin-3-yl)urea (8j)

$^1$H NMR (300 MHz, CDCl$_3$) δ 8.68 (d, J=2.5 Hz, 1H), 8.54 (d, J=2.2 Hz, 1H), 7.98 (d, J=8.1 Hz, 1H), 7.83 (s, 1H), 7.74 (d, J=8.0 Hz, 1H), 7.62-7.40 (m, 2H), 7.22-7.05 (m, 2H), 6.91 (dd, J=7.6, 2.0 Hz, 1H), 4.88 (s, 1H), 3.33 (t, J=6.4 Hz, 2H), 3.10 (s, 4H), 2.75 (s, 4H), 2.60-2.46 (m, 2H), 1.62 (d, J=7.3 Hz, 4H).

1-(4-(4-(2,4-dichlorophenyl)piperazin-1-yl)butyl)-3-(quinolin-3-yl)urea (8k)

$^1$H NMR (300 MHz, CDCl$_3$) δ 8.64 (d, J=2.6 Hz, 1H), 8.47 (d, J=2.3 Hz, 1H), 8.33 (s, 1H), 7.93 (d, J=8.3 Hz, 1H), 7.67 (dd, J=8.1, 1.2 Hz, 1H), 7.58-7.39 (m, 2H), 7.33 (d, J=2.4 Hz, 1H), 7.14 (dd, J=8.6, 2.4 Hz, 1H), 6.86 (d, J=8.7 Hz, 1H), 3.29 (s, 2H), 2.97 (s, 4H), 2.55 (s, 4H), 2.36 (s, 2H), 1.53 (s, 4H).

$^{13}$C NMR (75 MHz, CDCl$_3$) δ 156.07, 147.75, 144.08, 133.23, 130.25, 129.32, 128.55, 128.37, 128.23, 127.68, 127.58, 127.44, 127.23, 122.50, 121.00, 57.92, 53.10, 50.92, 40.08, 27.99, 24.02.

1-(4-(4-(4-chloro-2-fluorophenyl)piperazin-1-yl)butyl)-3-(quinolin-3-yl)urea (8m)

$^1$H NMR (300 MHz, CDCl$_3$:CD$_3$OD) δ 8.64 (d, J=2.1 Hz, 1H), 8.47 (d, J=2.4 Hz, 1H), 7.90 (d, J=8.3 Hz, 1H), 7.79-7.70 (m, 1H), 7.60-7.44 (m, 3H), 7.02 (dt, J=4.4, 2.1 Hz, 2H), 6.89 (t, J=8.8 Hz, 1H), 3.38-3.22 (m, 4H), 3.16-3.02 (m, 4H), 2.71 (s, 4H), 2.51 (t, J=7.2 Hz, 2H), 2.08-1.94 (m, 187), 1.68-1.53 (m, 187).

$^{13}$C NMR (126 MHz, CDCl$_3$:CD$_3$OD) δ 155.77, 155.25 (d, $J_{CF}$=250.0 Hz), 144.19, 144.08, 138.28 (d, $J_{CF}$=9.0 Hz), 133.22, 128.60, 127.51, 127.45, 127.34, 127.26, 127.12, 124.56 (d, $J_{CF}$=3.6 Hz), 122.18, 119.64 (d, $J_{CF}$=3.6 Hz), 116.89 (d, $J_{CF}$=24.3 Hz), 57.66, 52.89, 49.68, 49.66, 39.62, 29.68, 27.48, 23.38.

1-(4-(4-(2-fluoro-5-(trifluoromethyl)phenyl)piperazin-1-yl)butyl)-3-(quinolin-3-yl)urea (8n)

$^1$H NMR (300 MHz, CDCl$_3$) δ 8.65 (d, J=2.1 Hz, 1H), 8.52 (d, J=2.2 Hz, 1H), 8.04 (s, 1H), 7.97 (d, J=8.1 Hz, 1H), 7.72 (dd, J=8.1, 1.3 Hz, 1H), 7.59-7.42 (m, 2H), 7.19 (d, J=4.3 Hz, 1H), 7.15-7.03 (m, 2H), 3.32 (t, J=6.2 Hz, 2H), 3.22-2.99 (m, 4H), 2.73-2.58 (m, 4H), 2.45 (t, J=7.1 Hz, 2H), 1.69-1.47 (m, 4H).

$^{13}$C NMR (126 MHz, CDCl$_3$) δ 157.19 (d, J$_{CF}$=251.9 Hz), 155.99, 144.04 (d, J$_{CF}$=6.1 Hz), 140.22, 140.14, 133.32, 128.64, 128.43, 127.60, 127.48, 127.21, 127.01 (dq, J$_{CF}$=32.4, 4.0 Hz), 123.82 (q, J$_{CF}$=272.62 Hz), 122.31, 119.62 (m), 116.51 (d, J$_{CF}$=22.8 Hz), 116.03 (d, J$_{CF}$=3.9 Hz), 57.70, 52.81, 49.66, 49.63, 39.75, 27.66, 23.60.

1-(4-(4-(3-(trifluoromethyl)phenyl)piperazin-1-yl)butyl)-3-(quinolin-3-yl)urea (8p)

$^1$H NMR (300 MHz, CDCl$_3$) δ 8.66 (d, J=2.4 Hz, 1H), 8.49 (d, J=2.3 Hz, 1H), 8.09 (s, 1H), 7.95 (d, J=8.2 Hz, 1H), 7.70 (d, J=8.0 Hz, 1H), 7.60-7.42 (m, 2H), 7.33 (t, J=8.1 Hz, 1H), 7.07 (d, J=6.9 Hz, 2H), 7.00 (d, J=8.2 Hz, 1H), 3.30 (s, 2H), 3.25-3.11 (m, 4H), 2.66-2.51 (m, 4H), 2.39 (s, 2H), 1.56 (s, 4H).

$^{13}$C NMR (75 MHz, CDCl$_3$) δ 155.92, 151.05, 144.16, 144.11, 133.18, 131.37 (q, J$_{CF}$=31.8 Hz), 129.54, 128.57, 128.47, 127.80 (d, J$_{CF}$=271.8 Hz, CF$_3$), 127.66, 127.45, 127.22, 122.47, 118.65, 116.05, 116.00 (q, J$_{CF}$=3.8 Hz), 112.13 (q, J$_{CF}$=3.79 Hz), 57.84, 52.83, 48.31, 39.99, 27.88, 23.89.

1-(4-(4-(4-chlorophenyl)piperazin-1-yl)butyl)-3-(isoquinolin-3-yl)urea (11i)

$^1$H NMR (400 MHz, MeOD) δ 8.94 (s, 1H), 7.89 (d, J=8.2 Hz, 1H), 7.72 (d, J=8.3 Hz, 1H), 7.66-7.59 (m, 1H), 7.56 (s, 1H), 7.48-7.36 (m, 1H), 7.27-7.15 (m, 2H), 6.92-6.77 (m, 2H), 3.40 (t, J=6.0 Hz, 2H), 3.26-3.08 (m, 5H), 2.77-2.61 (m, 5H), 2.51 (d, J=7.2 Hz, 3H), 1.67 (d, J=3.3 Hz, 5H).

$^{13}$C NMR (101 MHz, MeOD) δ 156.40, 149.95, 149.60, 148.22, 138.33, 131.01, 128.87, 127.58, 125.86, 125.11, 124.88, 117.42, 104.92, 58.10, 52.80, 48.73, 27.88, 23.65.

Further, the dopamine D3 receptor-selective ligand having the major structure of Formula II was one selected from the group consisting of:

1-(benzothiazol-2-yl)-3-(4-(4-(4-chlorophenyl)piperazin-1-yl)butyl)urea (21i)

$^1$H NMR (300 MHz, DMSO-d$_6$) δ 10.64 (s, 1H), 7.86 (dd, J=7.9, 0.7 Hz, 1H), 7.61 (d, J=7.6 Hz, 1H), 7.42-7.29 (m, 1H), 7.28-7.13 (m, 3H), 6.99-6.84 (m, 2H), 6.79 (s, 1H), 3.18 (d, J=5.7 Hz, 2H), 3.12-3.01 (m, 4H), 2.53-2.44 (m, 6H), 2.33 (s, 2H), 1.49 (s, 4H).

$^{13}$C NMR (75 MHz, DMSO-d$_6$) δ 159.86, 153.78, 149.82, 149.00, 131.35, 128.55, 125.72, 122.55, 122.19, 121.29, 119.54, 116.70, 57.35, 52.55, 47.99, 27.37, 23.56.

1-(benzothiazol-2-yl)-3-(4-(4-(2,3-dichlorophenyl)piperazin-1-yl)butyl)urea (21j)

$^1$H NMR (300 MHz, CDCl$_3$) δ 7.79-7.68 (m, 2H), 7.45-7.34 (m, 1H), 7.30-7.19 (m, 2H), 7.19-7.02 (m, 2H), 6.93 (dd, J=7.2, 2.4 Hz, 1H), 3.44 (s, 2H), 3.07 (s, 4H), 2.67 (s, 4H), 2.50 (s, 2H), 1.69 (d, J=3.2 Hz, 4H).

$^{13}$C NMR (75 MHz, CDCl$_3$) δ 161.59, 154.68, 151.11, 133.98, 130.75, 127.42, 126.15, 124.58, 123.47, 121.26, 119.95, 118.57, 58.03, 53.24, 51.13, 40.07, 27.79, 24.06.

1-(benzothiazol-2-yl)-3-(4-(4-(2,4-dichlorophenyl)piperazin-1-yl)butyl)urea (21k)

$^1$H NMR (300 MHz, CDCl$_3$) δ 7.73 (dd, J=8.0, 1.3 Hz, 2H), 7.45-7.36 (m, 1H), 7.34 (d, J=2.4 Hz, 1H), 7.30-7.21 (m, 2H), 7.16 (dd, J=8.6, 2.5 Hz, 1H), 6.92 (d, J=8.6 Hz, 1H), 3.42 (d, J=6.2 Hz, 2H), 3.03 (s, 4H), 2.64 (s, 4H), 2.48 (t, J=6.9 Hz, 2H), 1.81-1.53 (m, 4H).

$^{13}$C NMR (75 MHz, CDCl$_3$) δ 161.59, 154.67, 149.26, 147.94, 130.78, 130.25, 129.36, 128.14, 127.57, 126.15, 123.48, 121.25, 121.07, 119.98, 58.04, 53.21, 51.07, 40.09, 27.81, 24.12.

1-(benzothiazol-2-yl)-3-(4-(4-(3-(trifluoromethyl)phenyl)piperazin-1-yl)butyl)urea (21p)

$^1$H NMR (300 MHz, CDCl$_3$) δ 7.73 (dd, J=8.0, 3.7 Hz, 2H), 7.46-7.22 (m, 3H), 7.14-6.96 (m, 3H), 3.44 (s, 2H), 3.35-3.19 (m, 4H), 2.76-2.58 (m, 4H), 2.51 (d, J=7.0 Hz, 2H), 1.69 (d, J=3.4 Hz, 4H).

In order to carry out biological activity tests, it is necessary to synthesize reference compounds.

At 0° C., EDCI and HOBT were slowly added to a solution of 1H-indole-2-carboxylic acid in DMF, 4-amino-1-butanol was added dropwise, slowly warmed to room temperature, and stirred overnight. When the reaction was completed as detected by TLC, the reaction was dispersed with water, and extracted with ethyl acetate. The solvent was recovered and the residue was separated by column chromatography to obtain compound 29. The hydroxy compound 29 was activated into mesylate or bromide and further reacted with 2,3-dichlorophenylpiperazine (or 2,4-dichlorophenylpiperazine) to produce reference compounds 31j and 31k.

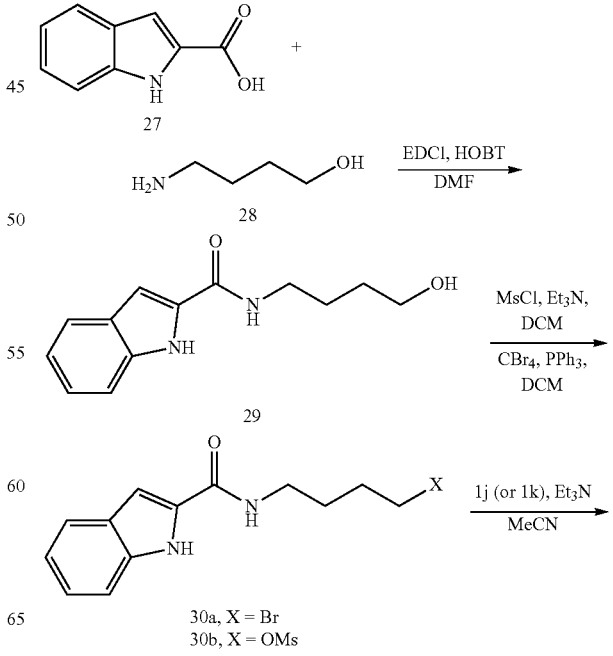

-continued

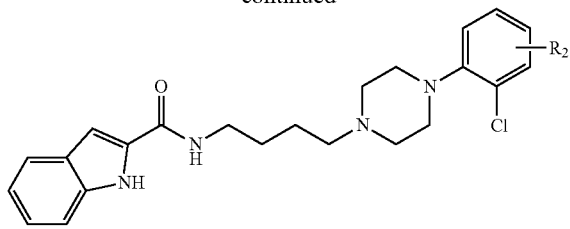

31j, R2 = 3-Cl
31k, R2 = 4-Cl

N-(4-(4-(2,3-dichlorophenyl)piperazin-1-yl)butyl)-1H-indole-2-carboxamide (31j)

Compound 31j was a colorless solid. Yield: 53%. $^1$H NMR (600 MHz, CDCl$_3$) δ 7.72-7.62 (m, 1H), 7.45 (dd, J=8.3, 0.8 Hz, 1H), 7.27 (ddd, J=8.2, 7.0, 1.1 Hz, 1H), 7.23-7.09 (m, 3H), 7.02 (s, 1H), 6.96 (dd, J=7.6, 2.0 Hz, 1H), 3.48 (t, J=6.3 Hz, 2H), 3.10 (s, 4H), 2.72 (s, 4H), 2.52 (d, J=7.0 Hz, 2H), 1.78-1.60 (m, 4H).
$^{13}$C NMR (151 MHz, CDCl$_3$) δ 162.22, 150.62, 136.31, 133.84, 130.63, 127.38, 127.33, 127.26, 124.68, 124.08, 121.65, 120.18, 118.45, 111.79, 103.05, 57.83, 53.02, 50.60, 39.03, 27.06, 23.61.

N-(4-(4-(2,4-dichlorophenyl)piperazin-1-yl)butyl)-1H-indole-2-carboxamide (31k)

Compound 31k was a colorless solid. Yield: 54%. $^1$H NMR (600 MHz, CDCl$_3$/CD$_3$OD 8:1) δ 7.69-7.61 (m, 1H), 7.45 (dd, J=8.3, 0.9 Hz, 1H), 7.36 (d, J=2.4 Hz, 1H), 7.27 (ddd, J=8.2, 7.0, 1.1 Hz, 1H), 7.20 (dd, J=8.6, 2.5 Hz, 1H), 7.12 (ddd, J=8.0, 7.0, 1.0 Hz, 1H), 7.05 (d, J=0.9 Hz, 1H), 6.97 (d, J=8.6 Hz, 1H), 3.47 (t, J=6.5 Hz, 2H), 3.06 (s, 4H), 2.68 (s, 4H), 2.55-2.39 (m, 2H), 1.66 (dt, J=11.8, 5.0 Hz, 4H). $^{13}$C NMR (151 MHz, CDCl$_3$/CD$_3$OD 8:1) δ 162.27, 147.40, 136.30, 130.56, 129.97, 129.10, 128.14, 127.39, 127.25, 123.93, 121.52, 120.89, 120.02, 111.69, 103.14, 57.82, 52.88, 50.44, 38.99, 27.03, 23.55.

The processes and results of bioactivity tests are as follows.

Competitive Inhibition Test Using Radioligands

Human embryonic kidney-293 cells were cultured in fresh MEM medium containing 10% fetal bovine serum, 100 units of penicillin, and 100 µg/mL streptomycin at 37° C. under 5% CO$_2$. Cells were transfected with DNA plasmids of dopamine D2 and D3 receptors respectively by using polyethylenimine. After transfection for 4 hours, medium was replaced with fresh MEM medium containing fetal bovine serum and the cells were further cultured for 24 hours. The cells were seeded into 24-well plates and cultured for 14-16 hours or overnight. After the medium was discarded, the cells were rinsed with pre-cooled serum-free MEM. Radioligand ([$^3$H]-sulpiride) and various concentrations of compounds were added into the adherent cells, and incubated in a bath at 4° C. for 150 minutes. The cells were rinsed three times with pre-cooled MEM containing 10 mM HEPES to remove unbound ligands. After the medium was completely removed, the cells were lysed with 1% sodium lauryl sulfate. The remaining radioligands were detected with a liquid scintillation counter to calculate the relative amount of bound compounds.

TABLE 1

Results of a competition assay using arylpiperazine-phthalimide compounds at a concentration of 100 nM and radioligands

| Compound | D3 Receptor Displacement (%) | D2 Receptor Displacement (%) |
| --- | --- | --- |
| 3a | 82.6 ± 2.7 | 31.8 ± 3.3 |
| 3c | 30.8 ± 14.3 | −6.3 ± 4.0 |
| 3d | 65.4 ± 5.8 | 17.7 ± 3.7 |
| 3e | 26.2 ± 2.7 | 4.8 ± 6.5 |
| 3f | 33.9 ± 6.0 | 10.3 ± 6.1 |
| 3g | 43.8 ± 4.5 | 28.7 ± 3.3 |
| 3h | 86.7 ± 1.4 | 64.8 ± 3.5 |
| 3i | 30.5 ± 12.8 | 59.2 ± 18.3 |
| 3i•HCl | 2.5 ± 1.5 | 16.3 ± 4.2 |
| 3j | 76.6 ± 3.1 | 70.3 ± 2.7 |
| 3k | N.D. | N.D. |
| 3k•HCl | 23.0 ± 8.2 | 30.2 ± 3.4 |
| 3m | 7.0 ± 4.6 | 2.8 ± 12.0 |
| 3n | 1.6 ± 8.6 | −4.7 ± 7.8 |
| 3p | 51.5 ± 3.3 | 44.0 ± 1.6 |
| 3p•HCl | 46.9 ± 1.3 | 37.9 ± 2.8 |
| sulpiride | 87.9 ± 1.8 | 92.2 ± 0.1 |

TABLE 2

Results of a competition assay using arylpiperazine-arylurea compounds at a concentration of 100 nM and radioligands

| Compound | D3 Receptor Displacement (%) | D2 Receptor Displacement (%) |
| --- | --- | --- |
| 7i | N.D | N.D |
| 7i•HCl | −4.5 ± 9.7 | 13.4 ± 8.5 |
| 8a | 88.4 ± 0.6 | 31.5 ± 9.2 |
| 8a•HCl | 86.6 ± 0.5 | 8.0 ± 9.7 |
| 8d | 76.4 ± 2.8 | 5.6 ± 8.5 |
| 8d•HCl | 88.1 ± 1.9 | 19.5 ± 8.8 |
| 8e | 66.9 ± 1.1 | 7.6 ± 6.1 |
| 8e•HCl | 88.8 ± 0.7 | −5.0 ± 17.8 |
| 8f | 70.1 ± 4.3 | 5.6 ± 8.5 |
| 8f•HCl | 32.0 ± 3.1 | −16.6 ± 6.8 |
| 8g | 81.0 ± 3.4 | 26.2 ± 6.3 |
| 8g•HCl | 87.8 ± 1.3 | 31.9 ± 5.1 |
| 8h | 73.4 ± 7.4 | 7.9 ± 5.2 |
| 8h•HCl | 76.8 ± 4.2 | −1.4 ± 14.8 |
| 8i | 80.0 ± 2.7 | 10.2 ± 6.7 |
| 8i•HCl | 75.0 ± 1.1 | 15.2 ± 1.6 |
| 8j•HCl | 26.6 ± 1.5 | 4.8 ± 4.3 |
| 8k | 39.7 ± 5.0 | −0.9 ± 6.3 |
| 8k•HCl | 58.2 ± 7.8 | −0.8 ± 1.6 |
| 8m | 79.5 ± 2.7 | 6.3 ± 11.2 |
| 8m•HCl | 79.5 ± 3.3 | −1.9 ± 8.5 |
| 8n | 73.2 ± 3.9 | 24.9 ± 1.8 |
| 8n•HCl | 72.3 ± 0.9 | 10.7 ± 4.0 |
| 8p | 11.4 ± 0.2 | −6.7 ± 4.2 |
| 8p•HCl | 92.4 ± 0.3 | 84.1 ± 1.8 |
| 11i | 11.3 ± 17.0 | −14.7 ± 1.8 |
| 21i | 49.0 ± 0.9 | 36.8 ± 6.5 |
| 21i•HCl | 19.5 ± 3.6 | 33.4 ± 5.9 |
| 21j | 61.5 ± 1.6 | 35.5 ± 3.4 |
| 21j•HCl | 63.8 ± 1.6 | 52.1 ± 2.0 |
| 21k | 40.6 ± 7.6 | 40.8 ± 5.6 |
| 21k•HCl | 36.6 ± 1.6 | 19.0 ± 1.4 |
| 21p | 44.0 ± 1.2 | 14.5 ± 3.9 |
| 21p•HCl | 50.0 ± 6.8 | 12.6 ± 2.5 |

Based on the screening performed at 100 nM, compounds with large differences in affinity for D3 receptors and D2 receptors were preferably further investigated for the dose-effect relationship to obtain their corresponding Ki values. All arylpiperazine-arylurea compounds had high affinity and selectivity for D3 receptors. Among them, 8i had a selectivity for D3 receptors of more than 10,000-fold, and had an affinity in nM level for D3 receptors. Its most commonly used pharmaceutical salt, hydrochloride, also had a high selectivity; its analogue, 8h, also had an extremely high selectivity—1924-fold; many analogues or derivatives had a selectivity of more than 100-fold. In comparison, reference compounds 31j and 31k had a weak affinity in the form of free alkaloids, and had increased affinity when prepared as hydrochlorides, but their selectivity for D3 receptors was 13-fold and 59-fold, respectively.

TABLE 3

Ki values and selectivities of arylpiperazine-phthalimide and arylpiperazine-arylurea compounds

| Compound | $Ki_{D3R}$ (nM) | $Ki_{D2R}$ (nM) | D2R/D3R |
|---|---|---|---|
| 3d | 19.3 | 2163.1 | 112 |
| 8a•HCl | 1.28 | 372.4 | 365.4 |
| 8d | 1.09 | 1346.1 | 1235 |
| 8d•HCl | 0.75 | 524.9 | 700 |
| 8e | 1.28 | 666.9 | 521 |
| 8e•HCl | 4.4 | 639.8 | 145.4 |
| 8f | 2.5 | 1746.1 | 698.4 |
| 8f•HCl | 6.87 | 1244.7 | 181.2 |
| 8g | 18.8 | 353.2 | 18.8 |
| 8h | 2.3 | 4426.6 | 1924 |
| 8i | 7.4 | >79629.6 | >10409 |
| 8i•HCl | 14.3 | 53097.6 | 3713 |
| 8k | 30.5 | 612.5 | 20 |
| 8m | 21.4 | 5943.9 | 277.8 |
| 8m•HCl | 14.0 | 1004.8 | 71.8 |
| 21p | 52.6 | 252.4 | 4.8 |
| 21p•HCl | 29.0 | 177.8 | 6.1 |
| 31j | 6207 | $ND^a$ | — |
| 31j•HCl | 15.6 | 202.3 | 13 |
| 31k | 497.6 | $ND^a$ | — |
| 31k•HCl | 407.2 | >23889 | >58.7 |

Intrinsic Functional Experiment of Compounds—a Luciferase Reporter Gene Assay

Human embryonic kidney-293 cells were transfected with complementary DNA of human dopamine D2, D3 and D4 receptors and a luciferase reporter gene transcriptionally controlled by CRE. The cells transfected with an empty vector were used as a negative control. The cells were seeded into 24-well plates, and 2 μM of forskolin and various concentrations of compounds were added. Cells added with quinpirole were used as a positive control group. After four hours' incubation, cells were lysed with cell lysis buffer for 20 minutes and then centrifuged. The supernatant was reacted with 25 μL of luciferase substrate and the expression level of luciferase was detected by using a dual luciferase reporter vector kit.

In the functional assay, compound 8i activated signaling pathways downstream of D3 receptors, acting similarly to quinpirole, but didn't activate signaling pathways downstream of D2 receptors and D3 receptors. It is therefore a functionally selective D3 receptor agonist that can be used as a molecular probe or a tool drug for investigating the physiological distribution and function of D3 receptors, D2 receptors, and D4 receptors, and mechanism of diseases associated with their functional disorders and dopamine metabolic disorders.

Effect of the D3 Receptor-Selective Ligand on Neuropsychosis

Experimental Sprague Dawley (SD) rats were randomly divided into an experimental group and a control group. After repeated behavior detection confirmed that there was no rotational behavior, the experiment was performed. Experimental group: rats were anesthetized with a mixture of xylazine (15 mg/kg, i.p.) and ketamine (100 mg/kg, i.p.), and then desipramine hydrochloride (25 mg/kg, s.c.) were used to protect noradrenergic neurons. 6 μg of 6-hydroxydopamine was dissolved in 2.3 μL of 0.9% sterile saline, and injected into the cerebral substantia nigra (antero-posterior −5.4 mm, midline-lateral ±8.1 mm and dorsal-ventral −1.8 mm from the bregma which was used as a zero coordinate) at a rate of 0.5 μL/min by using cerebral stereotaxic surgery. Rats in the control group were injected with the same dose of 0.9% sterile saline. After injection, the syringe needle was left in rats for 5 minutes before the needle was slowly withdrawn. After the rats awakened, they were placed in animal facilities for behavioral model evaluation to ensure that 6-hydroxydopamine induced the formation of a model with movement disorders and emotional/motivational disorders. Because hunger is prone to occur as a result of dopamine damage of the midbrain substantia nigra, 20% of rats were given high-calorie food for 1-2 weeks. After 19 days, the D3 receptor-selective ligand was continuously injected intraperitoneally for 3 days. Rats were allowed to accommodate the rotarod on days 19-20, and a rotarod assay was performed on days 21-22.

In the rotarod assay, the D3 receptor-selective agonist 8i increased the latency to fall in rats with Parkinson's disease induced by 6-hydroxydopamine, and reduced the frequency of falling in rats, and the hydrochloride of 8i significantly improved the motor dysfunction induced by neurotoxin 6-hydroxydopamine and had an effect comparable to the effect of apomorphine which was used as a positive control drug.

Solubility Assay of the D3 Receptor-Selective Ligand

TABLE 4

Solubility of compound 8i in anhydrous ethanol

| Solubility in ethanol | 10 mg/mL | 5 mg/mL | 3.3 mg/mL |
|---|---|---|---|
| 8i | − | − | + |

Note:
− indicates that the compound was un-dissolved or not completely dissolved,
+ indicates that the compound was completely dissolved

TABLE 5

Solubility of compound 8i•HCl in anhydrous ethanol

| Solubility in ethanol | 25.6 mg/mL | 12.8 mg/mL | 8.53 mg/mL | 6.4 mg/mL |
|---|---|---|---|---|
| 8i•HCl | − | − | − | + |

Note:
− indicates that the compound was un-dissolved or not completely dissolved,
+ indicates that the compound was completely dissolved As can be seen from the above two tables, the solubility of D3 receptor-selective ligand compound 8i in anhydrous ethanol was increased by at least 1 time when prepared into a hydrochloride salt.

TABLE 6

Solubility of compound 8i and hydrochloride thereof in water

| Solubility in water | 12 mg/mL | 6 mg/mL | 3 mg/mL | 1 mg/mL |
|---|---|---|---|---|
| 8i | − | − | − | + |
| 8i•HCl | + | + | + | + |

Note:
− indicates that the compound was un-dissolved or not completely dissolved,
+ indicates that the compound was completely dissolved As can be seen from the above table, the solubility of D3 receptor-selective ligand compound 8i in water was increased by at least 12 times when prepared into a hydrochloride salt.

The above disclosure is only a preferred example of the present disclosure, and of course, the scope of the present disclosure is not limited thereto. Those skilled in the art should understand that equivalent changes which are made according to the present disclosure to implement all or part of the process of the above examples are still within the scope of the present disclosure.

What is claimed is:

1. A dopamine D3 receptor-selective ligand comprising a major structure as following formula I or formula II:

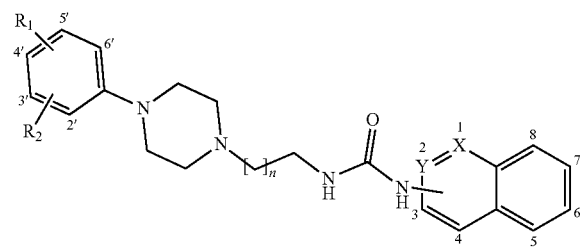

I wherein n=3 to 6;
X and Y are selected from C or N, and X and Y cannot be N or C at the same time, that is, the aromatic group attached to the urea functional group is quinolyl or isoquinolyl ring;
the urea group is located at 2- to 8-position of the quinolyl ring or at 1-, 3- to 8-position of the isoquinolyl ring;
R1 is selected from the group consisting of H, F, Cl, CF$_3$ and OMe, and R2 is selected from the group consisting of F, Cl, CF$_3$ and OMe;

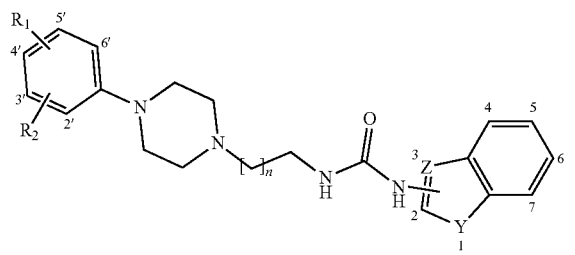

II wherein n=3 to 6;
Y is selected from NH or O or S; Z is selected from C or N, that is, the benzo 5-membered heterocyclic ring attached to the urea group is benzimidazole, benzothiazole, benzoxazole, benzothiophene, benzofuran or indole;
the urea is located at 2-position, or 4- to 7-position of a benzo 5-membered heterocyclic ring except at 4- to 7-position of benzothiazole;
R1 and R2 are each independently one selected from the group consisting of H, F, Cl and OMe.

2. The dopamine D3 receptor-selective ligand according to claim 1, wherein n=3 to 4.

3. The dopamine D3 receptor-selective ligand according to claim 1, wherein in formula I the urea group is located at 2-, 3-, 6-, 7-position of the quinolyl ring, or 3-, 6-, 7-position of the isoquinolyl ring, and in formula II the urea group is located at 2-, 5-, or 6-position of benzimidazole, benzoxazole, benzothiophene, benzofuran or indole, or at 2-position of benzothiazole.

4. A method for the prevention or treatment of neurodegenerative diseases, schizophrenia, anxiety, depression, drug addiction and drug dependence, comprising administrating the dopamine D3 receptor-selective ligand according to claim 1, or a pharmaceutical salt thereof, to a subject in need thereof.

5. A method for the prevention or treatment of Parkinson's disease, comprising administrating the dopamine D3 receptor-selective ligand according to claim 1, or a pharmaceutical salt thereof, to a subject in need thereof.

6. A method for the investigation of the D3R distribution and function of dopamine D2-like receptors, and for the elucidation of the mechanisms of disease associated with the dysfunction of dopamine D2-like receptors, comprising administrating the dopamine D3 receptor-selective ligand according to claim 1 to a subject, wherein the dopamine D3 receptor-selective ligand actss a molecular probe o investigate the distribution, activity, and function of dopamine D3R.

7. A method for the disease modification of hyperprolactinemia, extrapyramidal symptoms, or levodopa-related movement disorders, or dyskinesia, comprising administrating the dopamine D3 receptor-selective ligand according to claim 1, or a pharmaceutical salt thereof, to a subject in need thereof.

8. A dopamine D3 receptor-selective ligand, wherein the major structure is one selected from the group consisting of
1-(4-(4-(2,3-dichlorophenyl)piperazin-1-yl)butyl)-3-(quinolin-3-yl)urea;
1-(4-(4-(2,4-dichlorophenyl)piperazin-1-yl)butyl)-3-(quinolin-3-yl)urea;
1-(4-(4-(4-chlorophenyl)piperazin-1-yl)butyl)-3-(quinolin-3-yl)urea;
1-(4-(4-(3-chlorophenyl)piperazin-1-yl)butyl)-3-(quinolin-3-yl)urea;
1-(4-(4-(2-chlorophenyl)piperazin-1-yl)butyl)-3-(quinolin-3-yl)urea;
1-(4-(4-(2-fluorophenyl)piperazin-1-yl)butyl)-3-(quinolin-3-yl)urea;
1-(4-(4-(2,3-difluorophenyl)piperazin-1-yl)butyl)-3-(quinolin-3-yl)urea;
1-(4-(4-(2,4-difluorophenyl)piperazin-1-yl)butyl)-3-(quinolin-3-yl)urea;
1-(4-(4-(2,6-difluorophenyl)piperazin-1-yl)butyl)-3-(quinolin-3-yl)urea;
1-(4-(4-(4-chloro-2-fluorophenyl)piperazin-1-yl)butyl)-3-(quinolin-3-yl)urea;
1-(4-(4-(3-(trifluoromethyl)phenyl)piperazin-1-yl)butyl)-3-(quinolin-3-yl)urea;
1-(4-(4-(2-fluoro-5-(trifluoromethyl)phenyl)piperazin-1-yl)butyl)-3-(quinolin-3-yl)urea;
1-(4-(4-(4-chlorophenyl)piperazin-1-yl)butyl)-3-(quinolin-2-yl)urea;
1-(4-(4-(4-chlorophenyl)piperazin-1-yl)butyl)-3-(isoquinolin-3-yl)urea;
1-(benzothiazol-2-yl)-3-(4-(4-(2,3-dichlorophenyl)piperazin-1-yl)butyl)urea;
1-(benzothiazol-2-yl)-3-(4-(4-(2,4-dichlorophenyl)piperazin-1-yl)butyl)urea;

1-(benzothiazol-2-yl)-3-(4-(4-(4-chlorophenyl)piperazin-1-yl)butyl)urea; and 1-(benzothiazol-2-yl)-3-(4-(4-(3-(trifluoromethyl)phenyl)piperazin-1-yl)butyl)urea.

9. A method for the prevention or treatment of neurodegenerative diseases, schizophrenia, anxiety, depression, drug addiction or drug dependence, comprising administrating the dopamine D3 receptor-selective ligand according to claim 8, or a pharmaceutical salt thereof, to a subject in need thereof.

10. A method for the prevention or treatment of Parkinson's disease, comprising administrating the dopamine D3 receptor-selective ligand according to claim 8, or a pharmaceutical salt thereof, to a subject in need thereof.

11. A method for the investigation of the D3R distribution and function of dopamine D2-like receptors, and for the elucidation of the mechanisms of disease associated with the dysfunction of dopamine D2-like receptors, comprising administrating the dopamine D3 receptor-selective ligand according to claim 8 to a subject, wherein the dopamine D3 receptor-selective ligand acts as a molecular probe o investigate the distribution, activity, and function of dopamine D3R.

12. A method for the disease modification of hyperprolactinemia, extrapyramidal symptoms, or levodopa-related movement disorders or dyskinesia, comprising administrating the dopamine D3 receptor-selective ligand according to claim 8, or a pharmaceutical salt thereof, to a subject in need thereof.

* * * * *